(12) United States Patent
Giambattista

(10) Patent No.: US 12,133,971 B2
(45) Date of Patent: Nov. 5, 2024

(54) INJECTION DELIVERY DEVICE

(71) Applicant: L.G.P. Technology Holdings LLC, Cheyenne, WY (US)

(72) Inventor: Lucio Giambattista, Lighthouse Point, FL (US)

(73) Assignee: L.G.P. Technology Holdings LLC, Cheyenne, WY (US)

( * ) Notice: Subject to any disclaimer, the term of this patent is extended or adjusted under 35 U.S.C. 154(b) by 370 days.

(21) Appl. No.: 17/498,602

(22) Filed: Oct. 11, 2021

(65) Prior Publication Data

US 2022/0134006 A1 May 5, 2022

Related U.S. Application Data

(60) Provisional application No. 63/090,257, filed on Oct. 11, 2020.

(51) Int. Cl.
*A61M 5/24* (2006.01)
*A61M 5/31* (2006.01)
*A61M 5/32* (2006.01)

(52) U.S. Cl.
CPC ........ *A61M 5/2459* (2013.01); *A61M 5/2422* (2013.01); *A61M 5/3137* (2013.01); *A61M 5/3202* (2013.01); *A61M 5/3298* (2013.01)

(58) Field of Classification Search
CPC .............. A61M 5/2459; A61M 5/2422; A61M 5/3137; A61M 5/3202; A61M 5/3298; A61M 5/283
See application file for complete search history.

(56) References Cited

U.S. PATENT DOCUMENTS

| | | | |
|---|---|---|---|
| 1,747,243 A * | 2/1930 | Hoskins | A61M 5/24 604/233 |
| 6,039,713 A | 3/2000 | Botich et al. | |
| 2003/0199833 A1* | 10/2003 | Barker | A61M 5/283 604/110 |
| 2010/0262123 A1 | 10/2010 | Millerd | |
| 2014/0088512 A1 | 3/2014 | Quinn | |
| 2016/0354546 A1 | 12/2016 | Skufca et al. | |
| 2018/0147355 A1 | 5/2018 | Larsen et al. | |
| 2020/0316308 A1* | 10/2020 | Plumptre | A61M 5/3202 |
| 2020/0368445 A1* | 11/2020 | Weber | A61M 5/31585 |
| 2022/0249325 A1* | 8/2022 | Dittombee | A61M 5/2466 |
| 2023/0277780 A1* | 9/2023 | Fukuda | A61M 5/2422 604/117 |

* cited by examiner

*Primary Examiner* — Dung T Ulsh
(74) *Attorney, Agent, or Firm* — Weitzman Law Offices, LLC

(57) ABSTRACT

An injection delivery device involves a body, a medication-containing vial within at least a portion of the body, the medication-containing vial having an open end and a closed end opposite the open end. The open end of the vial includes a seal that prevents medication contained therein from exiting the vial until delivery of the medication to a target injection site is desired. The injection delivery device also includes a plunger positioned near the open end of the vial and a needle having a passage therethrough, wherein the needle, plunger and vial are positioned relative to each other such that, during delivery of an injection, a portion of the passage will be within the plunger, and the plunger and needle will remain stationary relative to each other while the vial moves relative the plunger in a direction towards the target injection site.

15 Claims, 19 Drawing Sheets

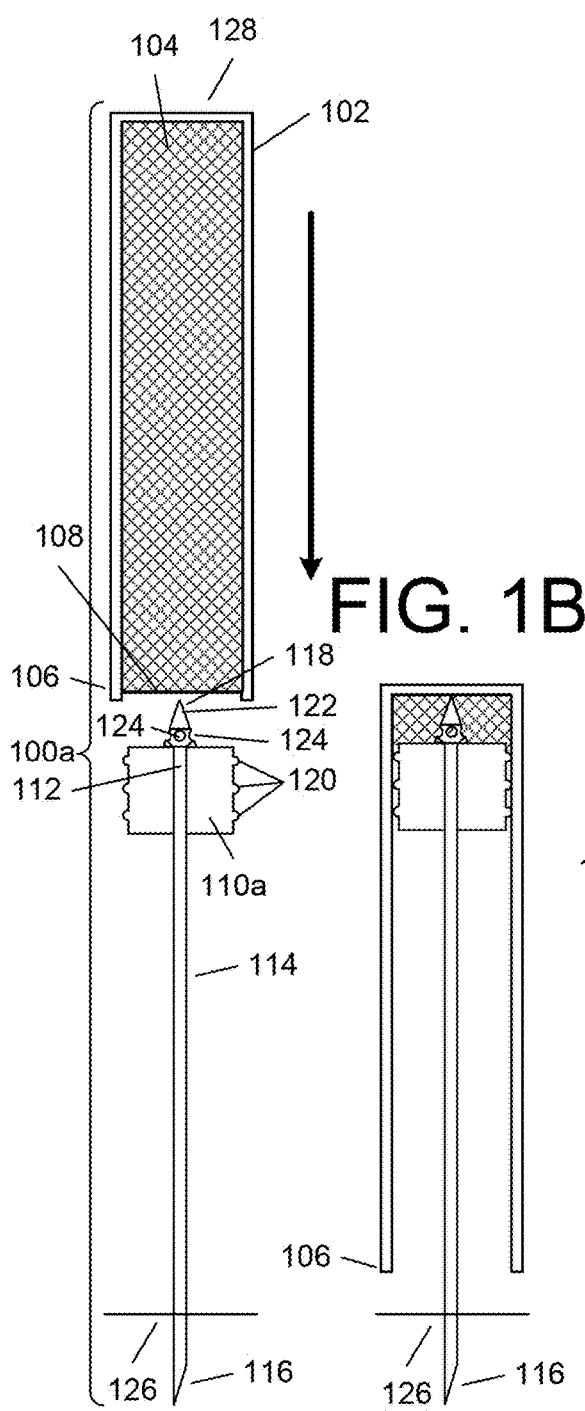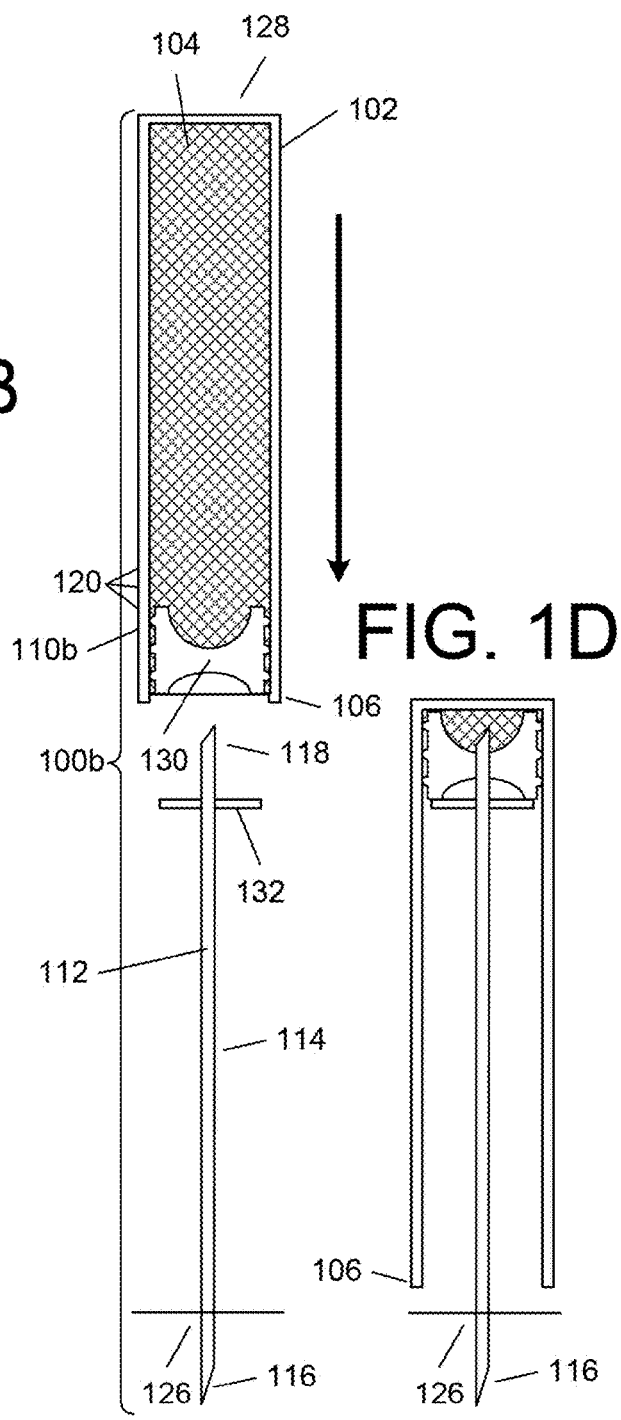
FIG. 1A  FIG. 1B  FIG. 1C  FIG. 1D

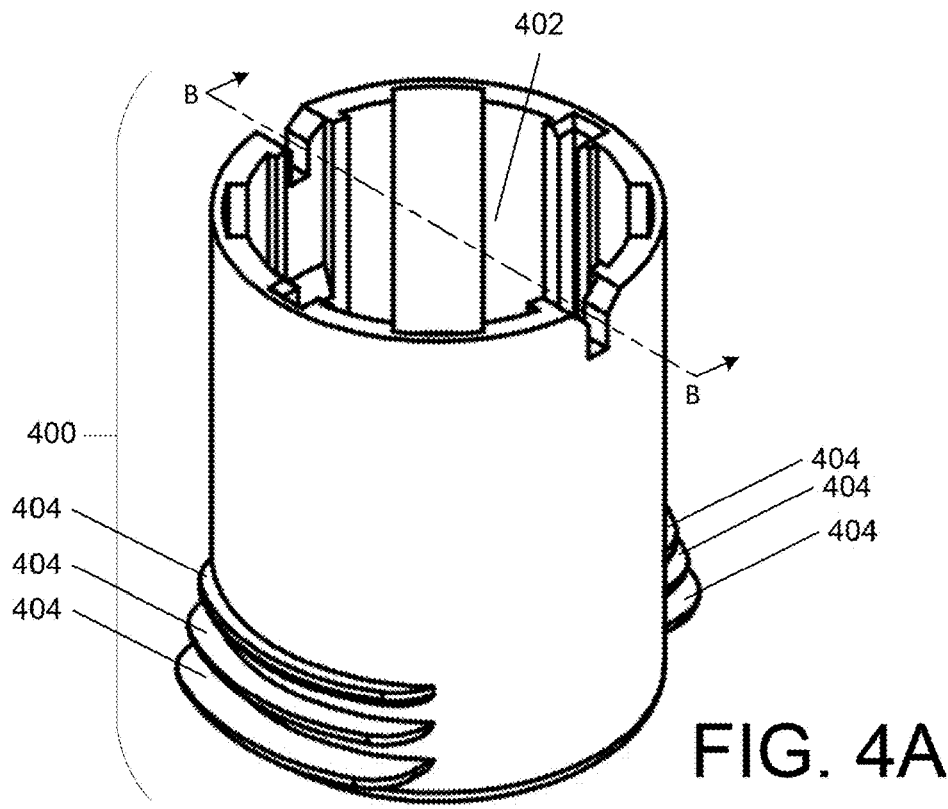
FIG. 4A
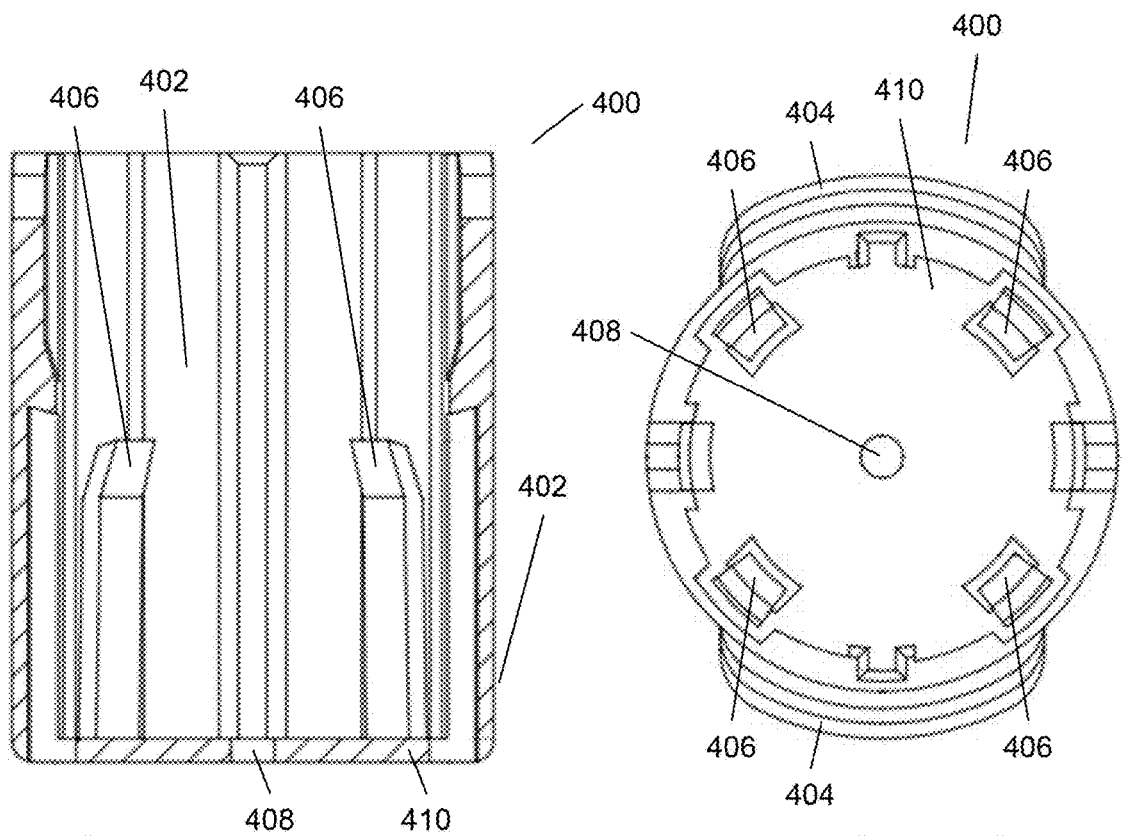
FIG. 4B
FIG. 4C

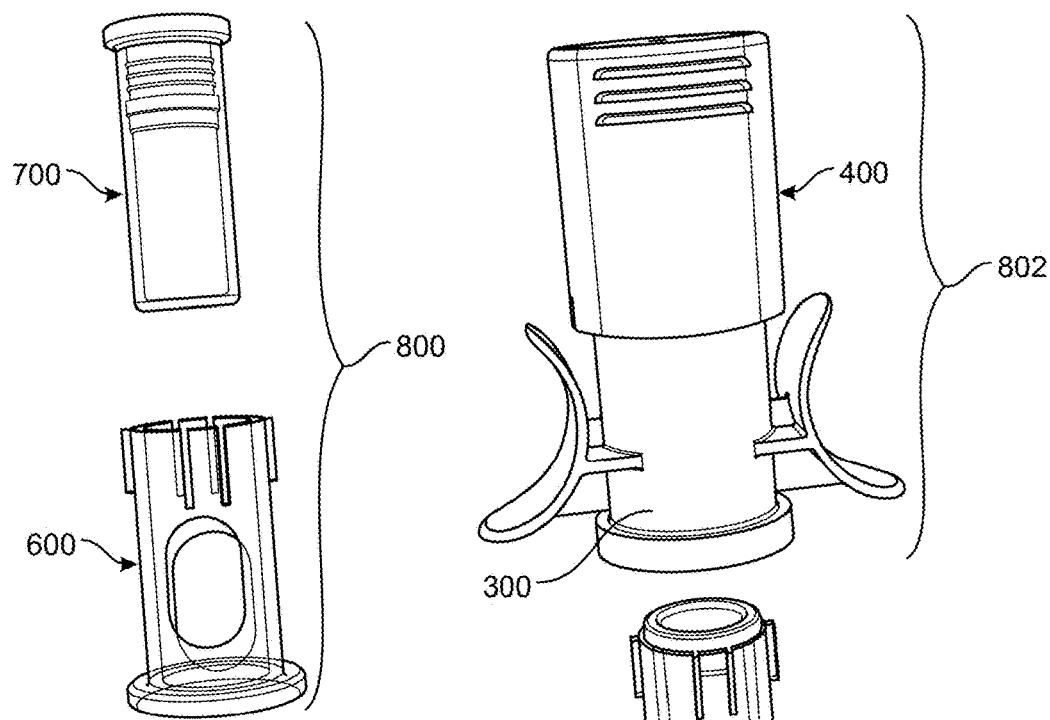
FIG. 8A
FIG. 8B
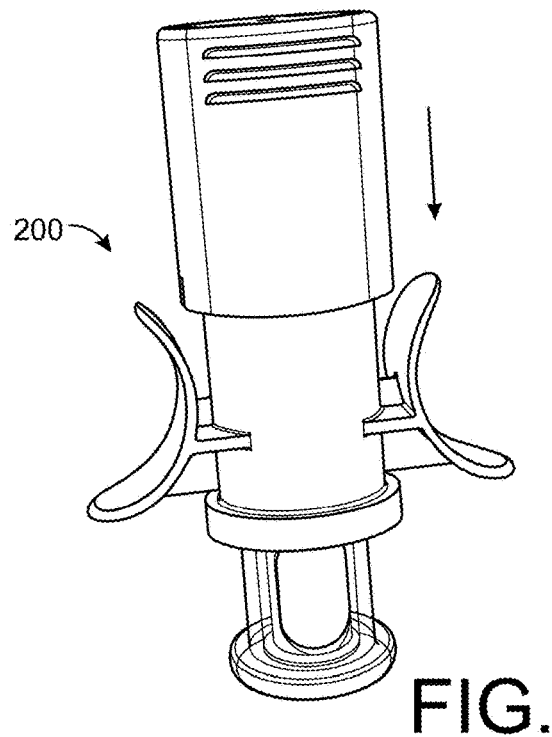
FIG. 8C

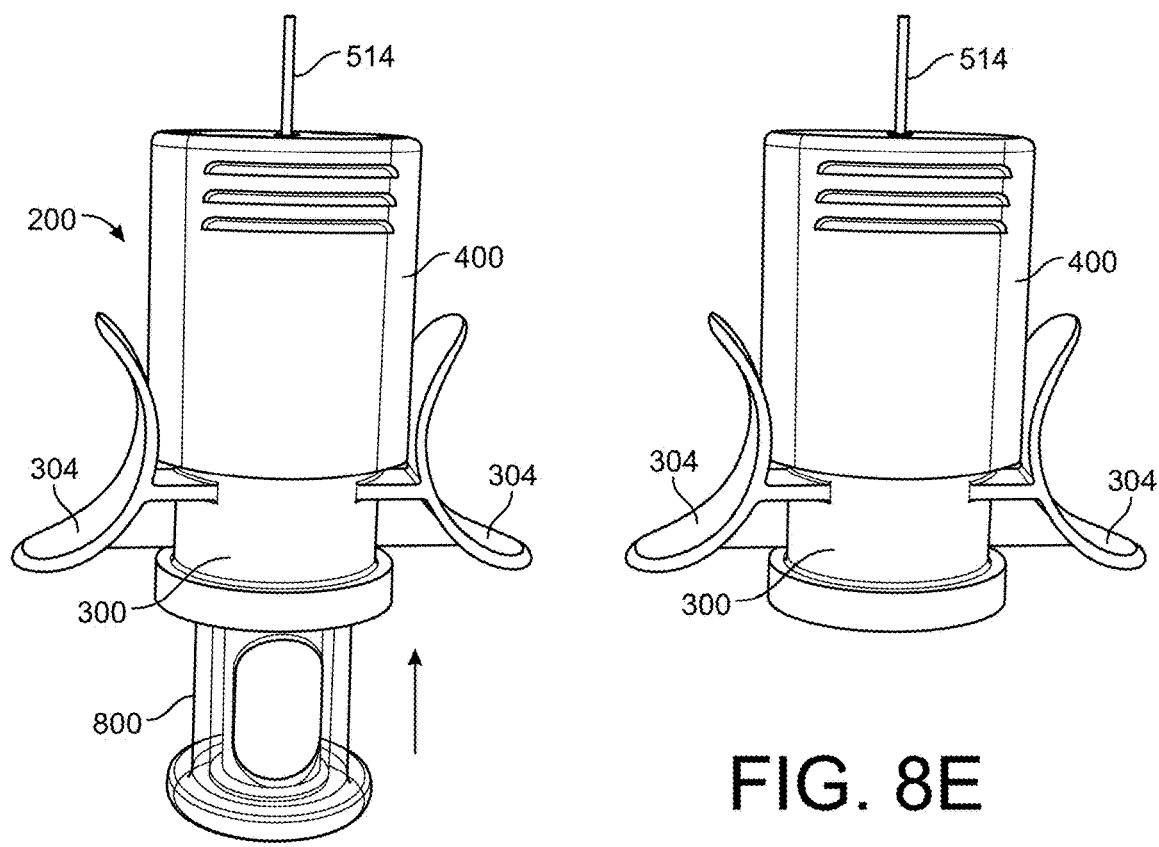
FIG. 8D
FIG. 8E
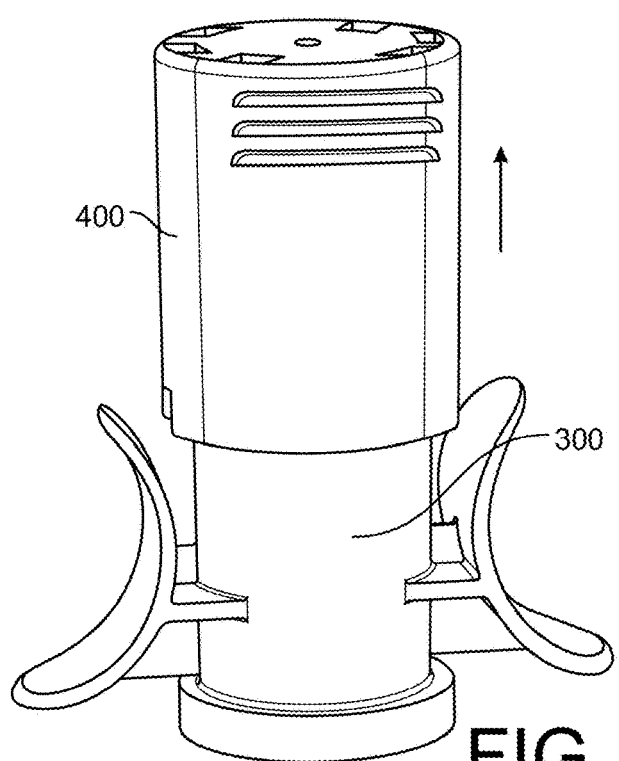
FIG. 8F

INJECTION DELIVERY DEVICE

CROSS REFERENCE TO RELATED APPLICATIONS

This application claims the benefit of U.S. Provisional Patent Application No. 63/090,257 filed Oct. 11, 2020, the entire disclosure of which is incorporated by reference as if fully set forth herein.

FIELD OF THE INVENTION

This disclosure relates generally to injection delivery devices, such as syringes and autoinjectors.

BACKGROUND

There are many medical contexts, including the delivery of a vaccine or an emergency dose of a medicine such as epinephrine, where it is advantageous to have a mass-produced, pre-filled injection delivery device, such a as a syringe or autoinjector, available when needed for future use.

A traditional syringe, when an injection is to be delivered, typically involves a glass vial containing specific liquid medicine (e.g., the body of a syringe or separate vial that has been loaded into a delivery device like an autoinjector), with the vial having a rubber stopper attached to a plunger at one end, and an opening to a cannula or needle at the other end. The syringe operates such that, when a human thumb or a component of an autoinjector depresses the plunger, the plunger presses against the liquid medicine within the vial causing the plunger to pass through the vial and thereby force the liquid medicine through the cannula or needle.

However, this type of design can shorten the shelf life of a medication due to exposure of the medication to either the metal of the needle or to the air, if the plunger seal is imperfect. One approach to improving the shelf-life involves use of non-reactive needle material or a more conservative construction that requires loading of the medication immediately prior to use. The former has an increased cost and the latter may not be practical in some cases.

Thus, there is a need for an injection delivery device design that allows for pre-loading of a medication while minimizing the opportunities for its contamination during storage in advance of use.

There is a further need for an injection delivery device design that is simple to use and inexpensive to manufacture.

SUMMARY

One aspect of this disclosure involves an injection delivery device including a body and a medication-containing vial within at least a portion of the body. The vial includes an open end and a closed end opposite the first end. The open end of the vial includes a seal that prevents medication contained therein from exiting the vial until delivery of the medication to a target injection site is desired. The injection delivery device also includes a plunger positioned near the open end of the vial, and a needle having a first end and a second end and a passage therethrough. The first end of the needle is usable for insertion into skin of a target injection site, and the second end of the needle is positioned to direct the medication from the vial into the passage for delivery to the target injection site via the first end. The needle, plunger and vial are positioned relative to each other such that, during delivery of an injection, a portion of the passage will be within the plunger, and the plunger and needle will remain stationary relative to each other while the vial moves relative the plunger in a direction towards the target injection site.

Another aspect of this disclosure involves an injection delivery device having a body, an insert within the body having a passage therethrough and a medication-containing vial within at least a portion of the body, the medication-containing vial having an open end and a closed end opposite the open end. The open end of the vial includes a seal that prevents medication contained therein from exiting the vial until delivery of the medication to a target injection site is desired. The injection delivery device also has a plunger positioned near the open end of the vial. The injection delivery device further has a first needle coupled to one end of the passage and a second needle coupled to an end of the passage opposite the one end. The first needle is positioned to be inserted into skin of a target injection site. The second needle is positioned to direct the medication from the vial into the passage for delivery to the target injection site via the first needle. The first and second needles, the plunger and the vial are positioned relative to each other such that, during delivery of an injection, a portion of the second needle will be within the plunger, and the plunger, the first needle and the second needle will remain stationary relative to each other while the vial moves relative the plunger in a direction towards the target injection site.

A further aspect of this disclosure involves an injection delivery device including an external subcomponent for constraining a needle which will deliver an injection to a target injection site, a plunger engagement feature within the external subcomponent, and having a passage therethrough, the plunger engagement feature for increasing pressure within a medication containing vial to cause medication to pass from the medication-containing vial to the needle via the passage, and an internal subcomponent for containing the medication containing vial and moving the medication containing vial relative to the plunger engagement feature of the external subcomponent and towards the target injection site.

Yet another aspect of this disclosure involves an injection delivery device having a plunger and needle on one side and medication within a vial on the other side, wherein the plunger and needle are positioned so that, at the start of an injection, the needle punctures the plunger so as to contact the medication and allow delivery of the medication to a target injection site through the plunger via the needle.

An additional aspect of this disclosure involves a method performed by an injection delivery device having a medication-containing vial having rigid walls and a distal end and a seal at a proximal end thereof. The method involves, in response to pressure applied to the distal end of the medication-containing vial, moving the vial in a direction towards an injection target site, so as to first cause a needle end to come into contact with medication in the medication-containing vial through piercing of the seal, and then, in response to continued pressure applied to the distal end moving the vial in the direction towards the injection target site so that the pressure causes the medication to be delivered to the target injection site via the needle as the distal end of the vial approaches the needle.

A still further aspect of this disclosure involves a method performed by an injection delivery device. The method involves moving a vial in a direction towards an injection target site to cause a stationary plunger to traverse the vial and thereby cause medication to be delivered to the target injection site through the plunger.

BRIEF DESCRIPTION OF THE DRAWINGS

This disclosure is further described in the detailed description that follows, with reference to the drawings, wherein like reference characters throughout the drawings refer to identical or, where a letter is appended functionally similar, elements throughout the separate views, and in which:

FIG. 1A illustrates, in simplified form, a cross section of a portion of one example implementation of an injection delivery device at a time ranging from during storage to immediately prior to initiating its use;

FIG. 1B illustrates, in simplified form, the portion of FIG. 1A after a pre-specified dose of the medication has been fully injected;

FIG. 1C illustrates, in simplified form, a cross section of a portion of an alternative example implementation an injection delivery device at a time ranging from during storage to immediately prior to initiating its use;

FIG. 1D illustrates, in simplified form, the portion of FIG. 1C after a pre-specified dose of the medication has been fully injected;

FIGS. 4A-4C are various views of a needle shield that, upon assembly, is coupled to the exterior subassembly of the manual injection syringe of FIG. 2;

FIGS. 8A-8F specifically depicts example processes for assembling and using the manual injection syringe of FIG. 2;

DETAILED DESCRIPTION

Figure 2:
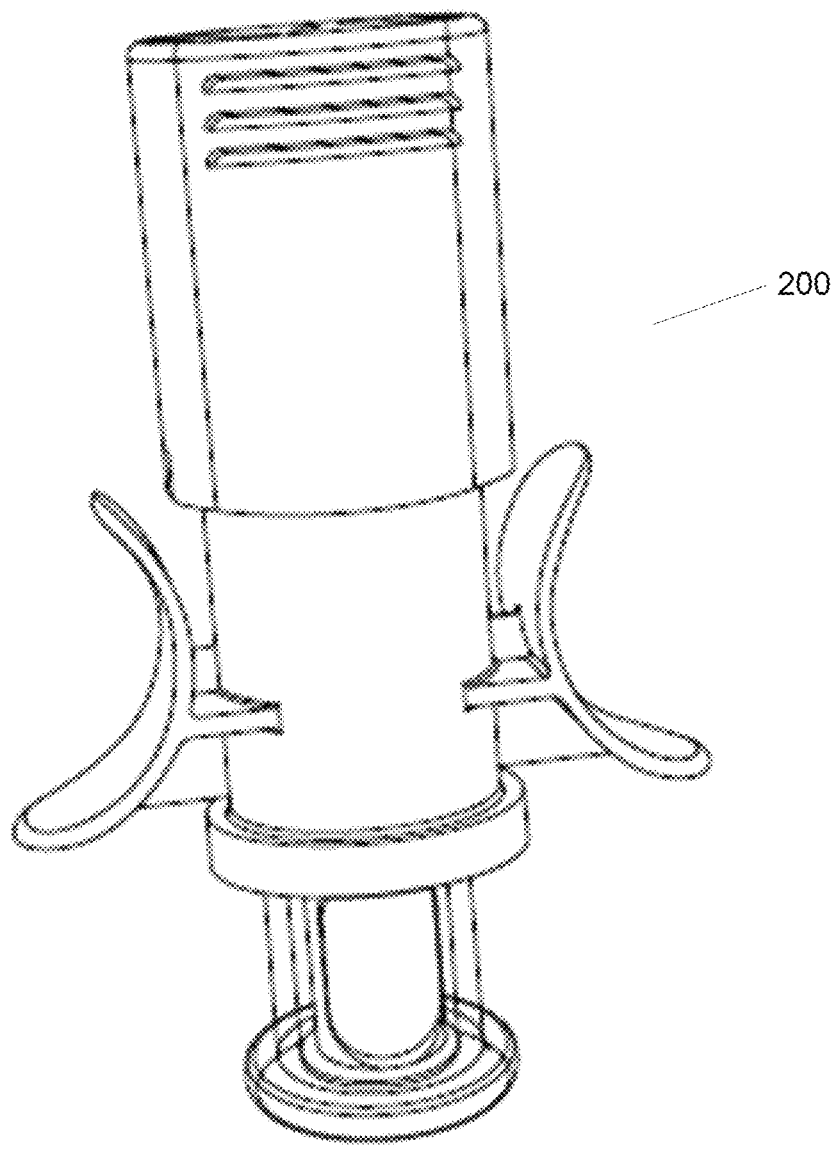
FIG. 2 is a perspective view of one example injection delivery device employing the teachings herein, in the form of a manual injection syringe.

In simplified overview, the injection delivery device designs described herein make use of a medication-containing vial that moves relative to the cannula or needle, which remains in place with respect to the injection target and delivers a medication directly from the vial to the target injection site. In addition, both the plunger and cannula/needle are located at the same end of the medicine-containing vial, unlike conventional syringes or autoinjectors, where the plunger and cannula/needle are on opposite ends of the medicine-containing vial. Still further, with the designs described herein, prior to the injection, the vial is completely sealed and the medication (e.g., drug, vaccine, hormones, etc.) does not come into contact with the cannula or needle until the injection is actually to be/being delivered. During delivery of the medication (i.e., the injection), the medication-containing vial moves towards the tip of the cannula or needle in the injection target such that, when the injection is complete, the end of the vial opposite the cannula or needle will have moved closer to both the tip of the cannula/needle and the injection target, and the plunger will be at or near the end of the vial that was opposite the cannula or needle prior to injection, even though the plunger will have remained stationary relative to the needle throughout delivery of the injection.

For purposes of simplicity, in the rest of the description that follows, the term "needle" will solely be used, but should be understood to be a definition that interchangeably encompasses a cannula and a needle. In addition, as used herein, the term "needle" is defined as being a non-coring needle when discussed in connection with piercing a seal or plunger.

The term "injection delivery device" as used herein means a single dose syringe or autoinjector, while specifically excluding large volume infusion pumps, patient-controlled analgesic infusion pumps and ambulatory infusion pumps.

In addition, for purposes of orientation, the terms "proximal" and "distal" should be understood to respectively be specifying linear placement relative to the injection target location and or tip of the needle therein during delivery of an injection. In other words the proximal end of any injection delivery devices described herein is the end closest to where the needle enters the skin of the injection target during administration the injection, and the distal end is the end of such injection delivery devices is the opposite end (i.e., the end most removed from the where the needle enters the skin of the injection target during administration the injection).

The foregoing will now be illustrated, in simplified form, with reference to FIGS. 1A-1D.

FIG. 1A illustrates, in simplified form, a cross section of a portion 100a of one example implementation of an injection delivery device, as will be described in greater detail herein, at a time ranging from during storage to immediately prior to initiating its use.

As shown in FIG. 1A, one part of the portion 100a involves a vial 102 that contains a medication 104 therewithin. The vial 102 only has an opening at one end 106. A seal 108, located at that end 106 maintains the medication 104 in the vial 102 until use and protects the medication 104 from contamination.

As further shown in FIG. 1A, another part of the portion 100a involves a plunger 110a containing a passage 112 that will, in use, allow medication to pass therethrough.

In the simplest case, the passage 112 may be part of a hollow injection needle 114 (a non-coring needle), to which the plunger 110a is affixed, the needle 114 having a first end 116, designed to pierce an injection target (the skin of the entity that will receive the injection) at a target injection site, and a second end 118, designed to pierce the seal 108 and through which the medication 104 in the vial 102 will enter the needle 114 on its way to the injection target.

In addition, depending upon the particular implementation, the plunger 110a may optionally include one or more features, e.g., sealing ring(s) 120 positioned to ensure that, during use, medication 104 only passes out of the vial 102 via the needle 114.

As further shown in FIG. 1A, optionally, instead of being a conventional angle-cut needle end, the second end 118 can be a type of spike 122 containing one or more holes 124 through which the medication 104 can pass into the passage 112.

In use, the vial 102 moves towards the plunger 110/needle 114 combination in the direction shown by the arrow. As the vial 102 moves, initially, the second end 118 (or spike 122) pierces the seal 108 and, as a result of continued movement, the stationary plunger 110a exerts a force on the medication 104, with the resulting pressure increase causing the medication 104 in the vial 102 to exit the only way it can, into the passage 112 and through the needle 114 towards the injection target 126.

FIG. 1B illustrates, in simplified form, the portion 100a of FIG. 1A after a pre-specified dose of the medication has been fully injected. As shown in FIG. 1B, the vial 102 has moved to a terminal position (i.e., a position where, depending upon the particular implementation, an end 128 of the vial 102 opposite the end 106 cannot move any further because, for example, the end 128 has bottomed out against the second end 118 (or spike 122) of the needle 114 or the plunger 110a, or the end 106 is prevented by some other feature of the overall device (not shown) from moving any further).

FIG. 1C illustrates, in simplified form, a cross section of a portion 100b of an alternative example implementation an injection delivery device, as will be described in greater detail herein, at a time ranging from during storage to immediately prior to initiating its use.

The portion 100b of FIG. 1C is similar to FIG. 1A, except that, in FIG. 1C, the plunger 110b is part of the vial 102 and serves a dual role of having a portion that acts as the seal 108 of FIG. 1A, while the rest of plunger 110b acts as the plunger 110a of FIG. 1A. In addition, unlike FIG. 1A, the second end 118 of the needle 114 is a conventional angle cut type needle end, which may have the same angle as the first end 116 or a different angle, the angle of the second end 118 being determined, as a matter of design choice, based upon the plunger 110b it will interact with. The plunger 110b also is constructed such that it has a thin area 130 where the needle 114 will pierce to make it easier for the needle 114 to do so. Finally, as shown in FIG. 1C, a plunger engagement feature 132 of some sort, for example, a plate, protrusion or expanded region of or on the needle, or an upstanding post, is associated with the needle 114 and is positioned to initially engage the plunger 110b, as the vial 102 is moved (in the direction of the arrow) during administration of the injection, and thereby, upon/following engagement, cause the plunger to remain in place (i.e., prevent the plunger from moving down the needle 114 as the vial 102 moves towards the injection target 124.

FIG. 1D illustrates, in simplified form, the portion 100b of FIG. 1C after a pre-specified dose of the medication has been fully injected.

As shown in FIG. 1D, the vial 102 has moved to its terminal position, in this example, where the end 128 of the vial 102 opposite the end 106 cannot move any further because the end 128 has bottomed out against the plunger 110b.

Based upon the foregoing, it should be apparent how the fundamental internal structure of devices constructed and operating according to the teachings herein are different from that of conventional syringes and autoinjectors.

FIG. 2 is a perspective view of one example injection delivery device 200 employing the teachings herein, in the form of a manual injection syringe made up of a body and a needle shield.

FIGS. 3A-3E are various views of an exterior subassembly 300 of the manual injection syringe 200 of FIG. 2.

Figure 3A:
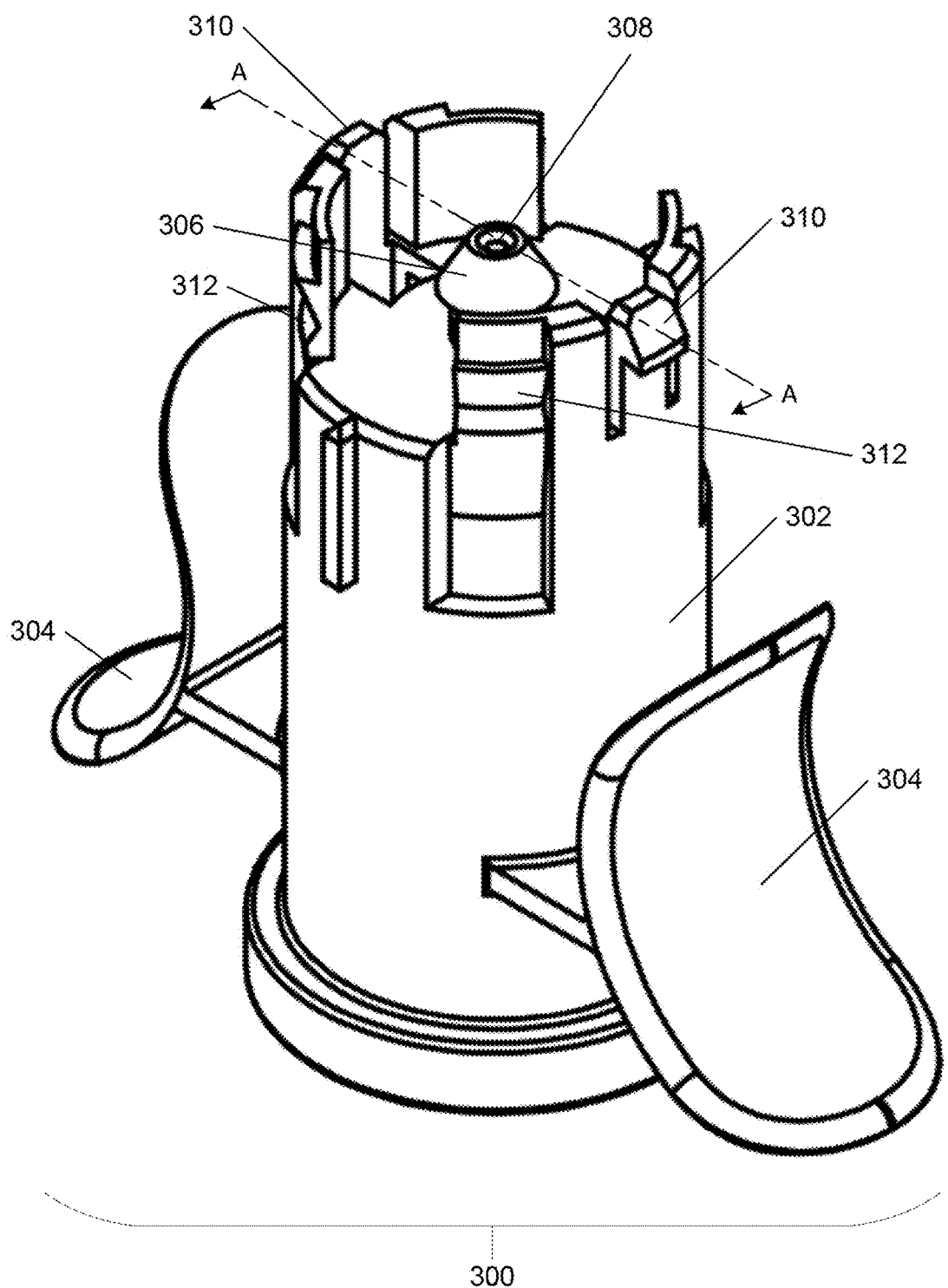
FIGS. 3A-3E are various views of an exterior subassembly 300 of the manual injection syringe of FIG. 2.

Specifically, FIG. 3A is a perspective view of the exterior subassembly 300. As is visible in FIG. 3A, the exterior subassembly 300 typically includes a generally cylindrical exterior surface 302 (although the exterior surface can be other shapes, the shape of the exterior surface 302 generally being a matter of design choice rather than function).

The exterior subassembly 300 shown further includes two or more finger grips 304 and a coupling 306 having an aperture 308. The coupling 306 is shaped to complementarily have a needle connect to it.

Additionally, the exterior subassembly 300 includes a proximal lip 310 which prevents removal of an attached needle shield from the exterior subassembly 300 when part of the assembled manual injection syringe 200. The exterior subassembly 300 also includes one or more proximal indentations 312 which, as explained in greater detail below, are used to capture and retain the needle shield in place, when it has been fully extended, to cover or otherwise enclose the needle of the manual injection syringe 200 following injection.

Figure 3B:
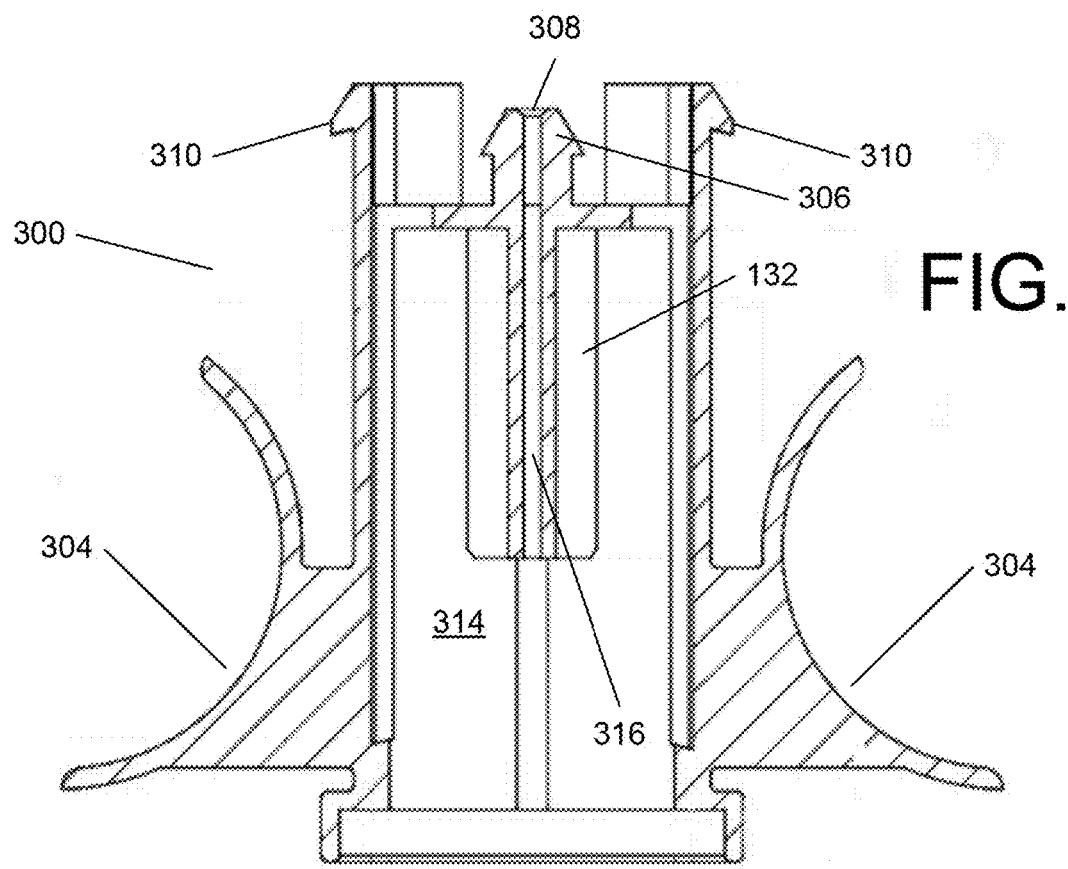

FIG. 3B is a cross section of the exterior subassembly 300 of FIG. 3A taken at A-A of FIG. 3A. As can now be seen, the exterior subassembly 300 includes a cavity 314 shaped to receive an interior subassembly therein as will described below. A passage 316 is coupled to the aperture 308 so that medication can pass from a vial within the manual injection syringe 200 to the needle connected to the coupling 306. The exterior subassembly 300 further includes a plunger engagement feature 132 (which may itself be a plunger, as in FIGS. 1A-1B), but as shown, is in the form of an "X" shaped riser that extends into the cavity 314 from near the coupling 306 and would engage a plunger that is used to seal a vial (e.g., as shown in FIG. 1C-1D).

Figure 3C:
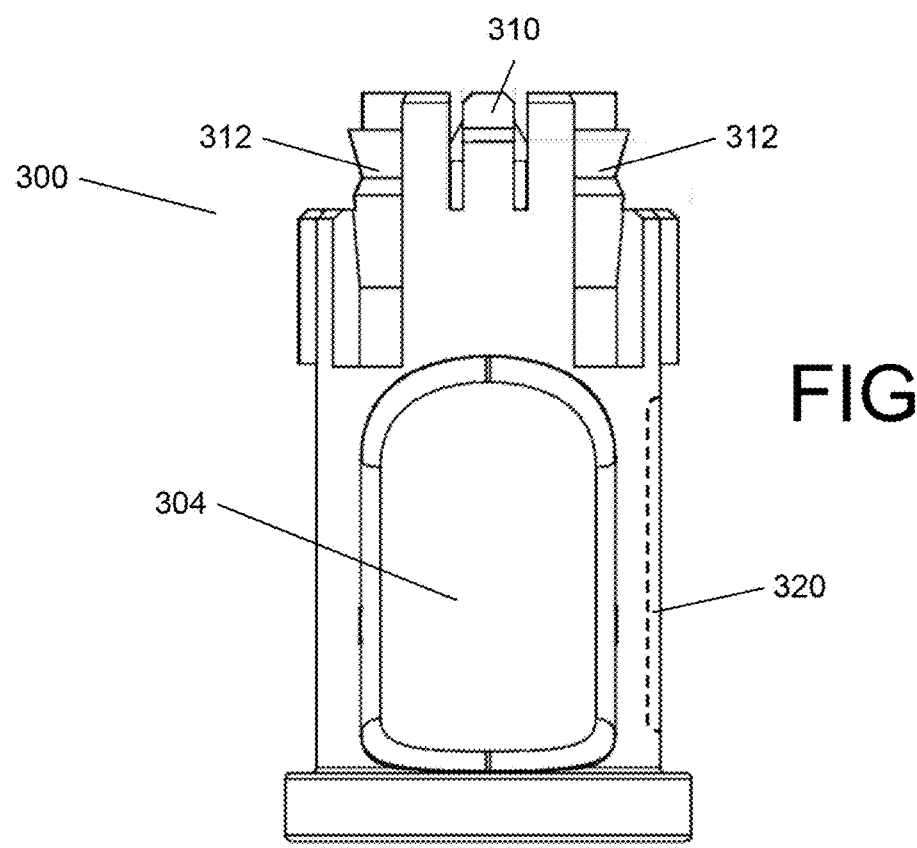

FIG. 3C is a side view of the exterior subassembly 300 of FIG. 3A. Depending upon the particular implementation, the exterior subassembly 300 may include one or more optional windows or openings 320, only part of which is shown in FIG. 3C. Depending upon placement and size, the one or more optional windows or openings 320 (shown with dashed lines) can be present to allow, for example, for verification that an interior subassembly has been properly inserted, verification that there is medication in a vial of the assembled manual injection syringe 200, and/or to determine or view the amount of medication (i.e., fluid level) therewithin.

Figure 3D:
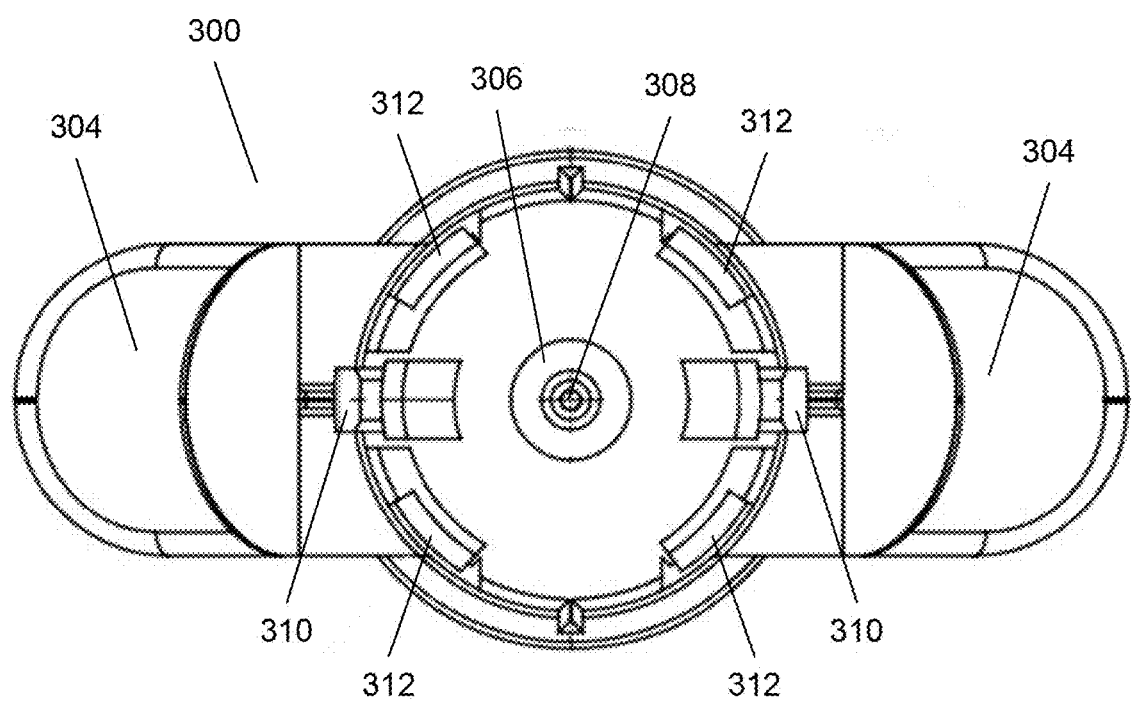

FIG. 3D is a top view of the exterior subassembly 300 of FIG. 3A.

Figure 3E:
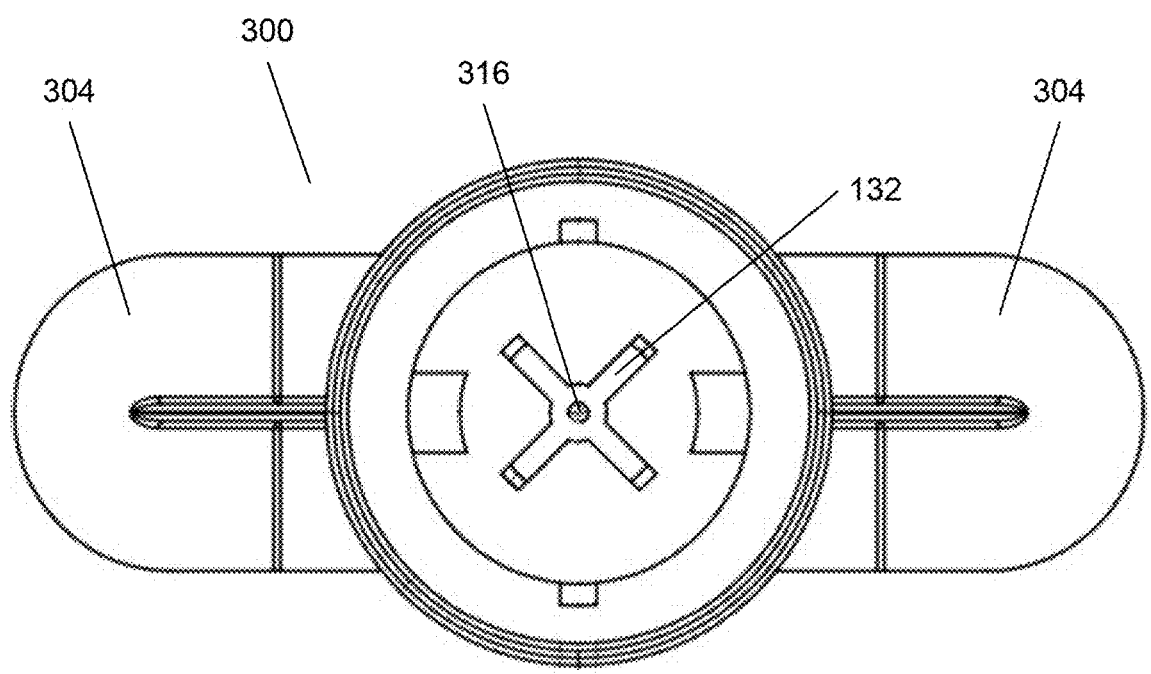

FIG. 3E is a bottom view of the exterior subassembly 300 of FIG. 3A.

In FIGS. 3A-3E, various additional features are shown, for example standoffs for the finger grips 304, as well as other detents and/or lips. However, since those features will be a matter of a particular implementation, and are not required for understanding or implementation of the teachings herein, their description is being omitted.

FIGS. 4A-4C are various views of a needle shield 400 that, upon assembly, is coupled to the exterior subassembly 300 of the manual injection syringe 200 of FIG. 2.

FIG. 4A is a perspective view of the needle shield 400.

As shown in FIG. 4A, the needle shield 400 is cylindrical (although, as with the exterior subassembly 300, other shapes can be used) and has an interior cavity 402 whose surface is shaped to correspond to part of the exterior surface 302 of the exterior subassembly 300, so that it may slide proximally or distally along that part of the exterior surface 302 of the exterior subassembly 300.

The needle shield 400 may optionally also include one or more surface features 404, such as a roughened area, ridges or fins, that allow a user to better grip the needle shield 400 and slide it proximally from a retracted position to an extended position, following injection, so that the needle shield 400 will enclose the needle and where it will be locked in place.

FIG. 4B is a cross section of the needle shield 400 of FIG. 4A taken at B-B of FIG. 4A.

As shown in FIG. 4B, within the interior cavity 402 of the needle shield 400 are one or more (as shown, four) interior fingers 406. The interior fingers 406 are positioned to correspond to the proximal indentations 312 of the exterior subassembly 300 and constructed to be in tension when abutting the exterior surface 302 of the exterior subassembly such that, when the interior fingers 406 are positioned over the proximal indentations 312 of the exterior subassembly 300, the tension will cause the interior fingers 406 to engage with the proximal indentations 312 on the exterior subassembly 300 to lock the needle shield 400 in place covering the needle. This is accomplished when the user pulls the needle shield 400 in the proximal direction.

FIG. 4C is a bottom view of the needle shield 400 of FIG. 4A, which provides a better view of the needle port 408 and the proximal surface 410 of the needle shield 400.

Figure 5:
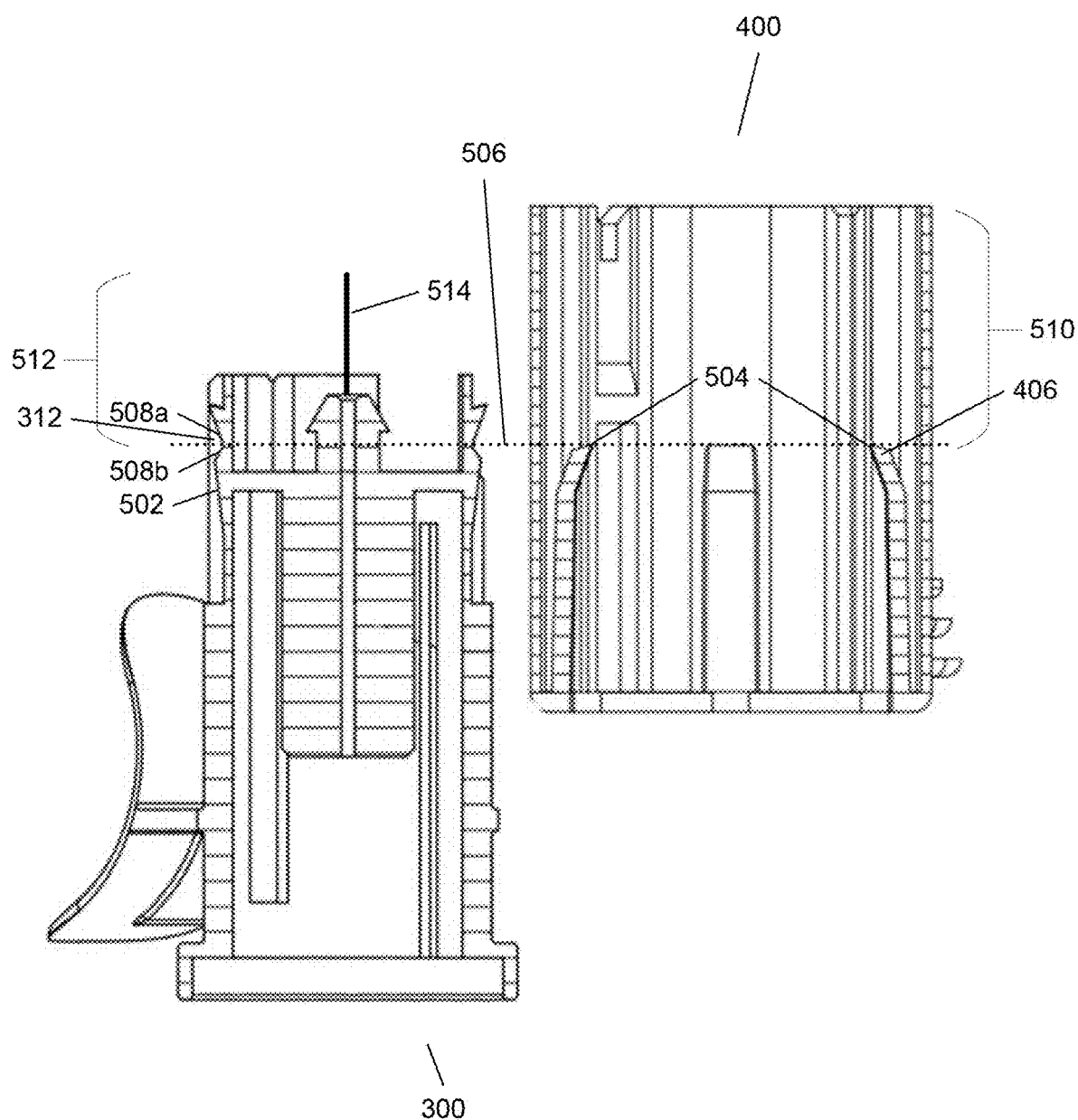
FIG. 5 illustrates, in simplified cross section form, how the needle shield and exterior subassembly lock together to secure the needle, post-injection.

The locking aspect between the needle shield 400 and exterior subassembly 300 is shown in greater detail in FIG. 5, which illustrates, in simplified cross section form, how the two lock together to secure the needle, post-injection.

Specifically, when the needle shield 400 is moved proximally, the interior fingers 406 of the needle shield 400 move along a ramp-like surface 502 of the exterior subassembly 300, causing the interior fingers 406 to flex outward from their normal position until they align with the proximal indentations 312 of the exterior subassembly 300. At that point, due to the tension, the ends 504 of the interior fingers 406 of the needle shield 400 will return to their normal position, placing them within the proximal indentations 312 and locking the needle shield 400 in place.

When the needle shield 400 is moved distally, the needle will be exposed via a needle port 408 in the proximal surface 410 of the needle shield 400.

At this point, it should be recognized that, while with this example implementation, the proximal indentations 312 are part of the exterior subassembly 300 and the interior fingers 406 are part of the needle shield 400, other designs could have their interior fingers on the exterior subassembly and the proximal indentations on the needle shield. Moreover, other implementations could be constructed so that there is only one proximal indentation, for example, a single internally surrounding indented ring.

Continuing with FIG. 5, the dotted line shown therein specifies the relative positions of the common locking point between the exterior subassembly 300 and needle shield 400 when they would actually be fitted together. Thus, at any point below the dotted line 506, the tips of the interior fingers 406 of the needle shield 200 are unable to grasp any surface features of the exterior subassembly 300. As discussed above, at the dotted line 506, the interior fingers 406 engage the proximal indentations 312 formed near the proximal end of the exterior subassembly 300 and thereby resist movement of the needle shield 400 relative the exterior subassembly 300 in either the proximal or the distal direction, due to both the inward tension of the interior fingers 406 and the locally increasing radius of portions 508a, 508b of the exterior subassembly 300 in either direction from the proximal indentations 312.

In addition, as long as the longitudinal height of the part 510 of needle shield 400 above the dotted line 506 (i.e., between the proximal upper limit of the needle shield 400 and the locking part of the interior fingers 406) is greater than the longitudinal distance 512 between the same dotted line 506 (i.e., the locking part of the proximal indentations 312) and the proximal tip of a needle 514 attached to the exterior subassembly 300, the needle shield 400 will completely enclose the needle 514 for safety purposes.

FIGS. 6A-6D are various views of an interior subassembly 600 that, upon assembly, is coupled to, and partly within, the exterior subassembly 300 of the manual injection syringe 200 of FIG. 2.

Figure 6A:
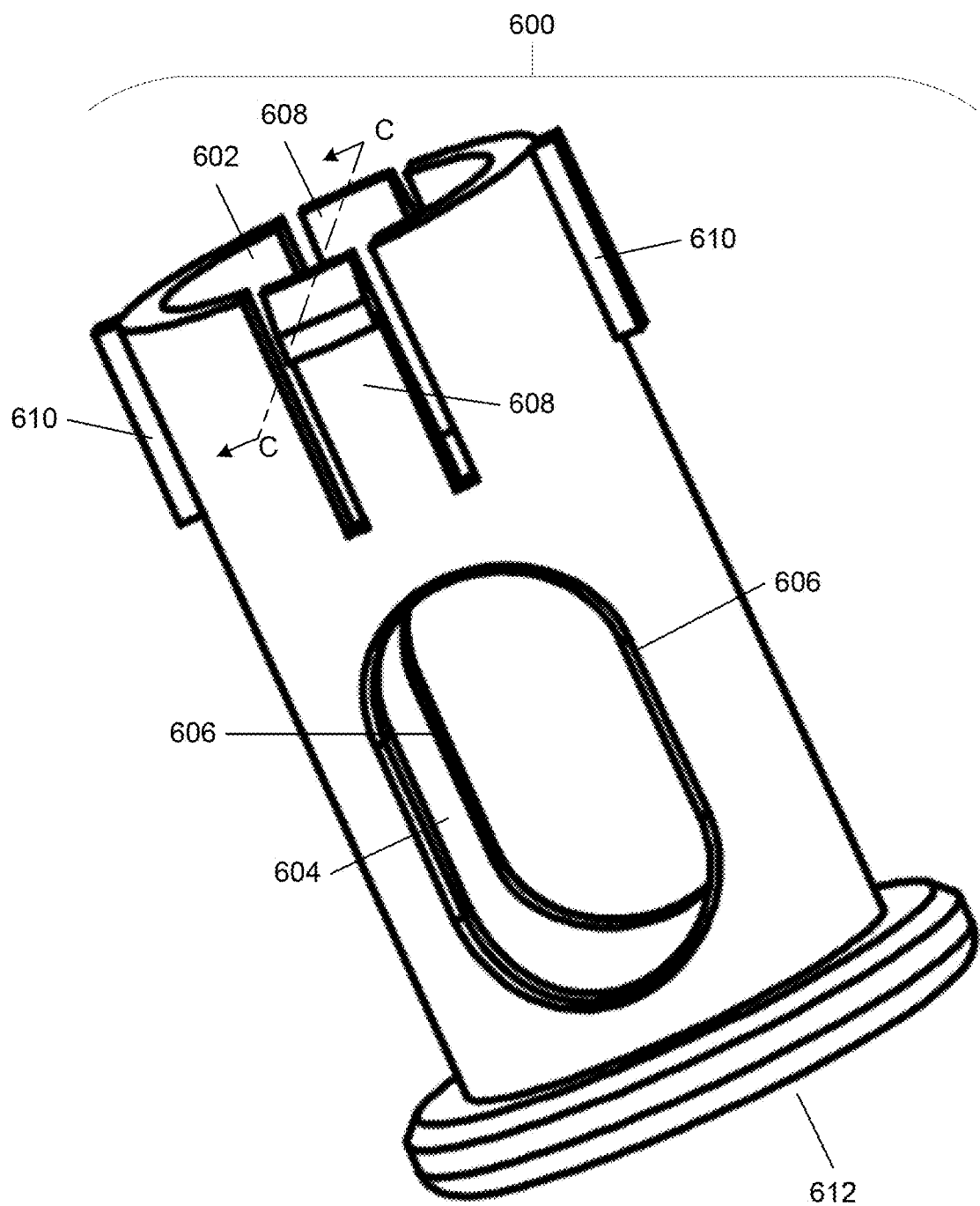
FIGS. 6A-6D are various views of an interior subassembly that, upon assembly, is coupled to, and partly within, the exterior subassembly of the manual injection syringe of FIG. 2.

Specifically, FIG. 6A is a perspective view of the interior subassembly 600.

As shown in at least FIG. 6A, the interior subassembly 600 includes a cavity 602, into which a vial 102 of medication is inserted during assembly and thereafter retained within the assembled manual injection syringe 200. The surface 604 defining the cavity 602 of the interior subassembly 600 may optionally include one or more features, such as roughened areas, internal ribs or certain surface types or materials or other physical features that generate friction against the vial 102 to keep the vial in place following insertion into the cavity 602.

The interior subassembly 600 may also optionally include one or more windows 606 positioned to correspond to the window(s) 320 of the exterior subassembly 300 and thereby permit viewing part of the vial 102 and/or its contents when the manual injection syringe 200 is fully assembled.

Still further, the interior subassembly 600 includes one or more retaining features, for example, flexible tabs 608 that are positioned to slot into a corresponding channel of the exterior subassembly 300 to prevent or inhibit removal of the interior subassembly 600 from the exterior subassembly 300 once the two are connected together, to allow for linear motion of the interior subassembly 600 relative to the exterior subassembly 300 (in a proximal direction during injection), and further, ideally (but not necessarily), to prevent the interior subassembly 600 from rotating relative to the exterior subassembly 300 about their common longitudinal axis, for example, to make sure that the optional windows 606, 320 remain substantially longitudinally aligned (i.e., within the tolerance needed to allow the linear motion of the interior subassembly 600 relative to the exterior subassembly 300 during injection).

Additionally, or alternatively, the interior subassembly 600 may optionally include one or more ribs or other features 610 that slot into a corresponding linear recess in the exterior subassembly 300 (or vice versa) that, along with, or instead of, the tabs 608, constrain motion of the interior subassembly 600, relative to the exterior subassembly 300, to linear motion (in a proximal direction during injection).

Finally, the distal end 612 of the interior subassembly 600 is constructed for application of force by a thumb of a user to activate/initiate an injection using the fully assembled manual injection syringe 200.

Figure 6B:
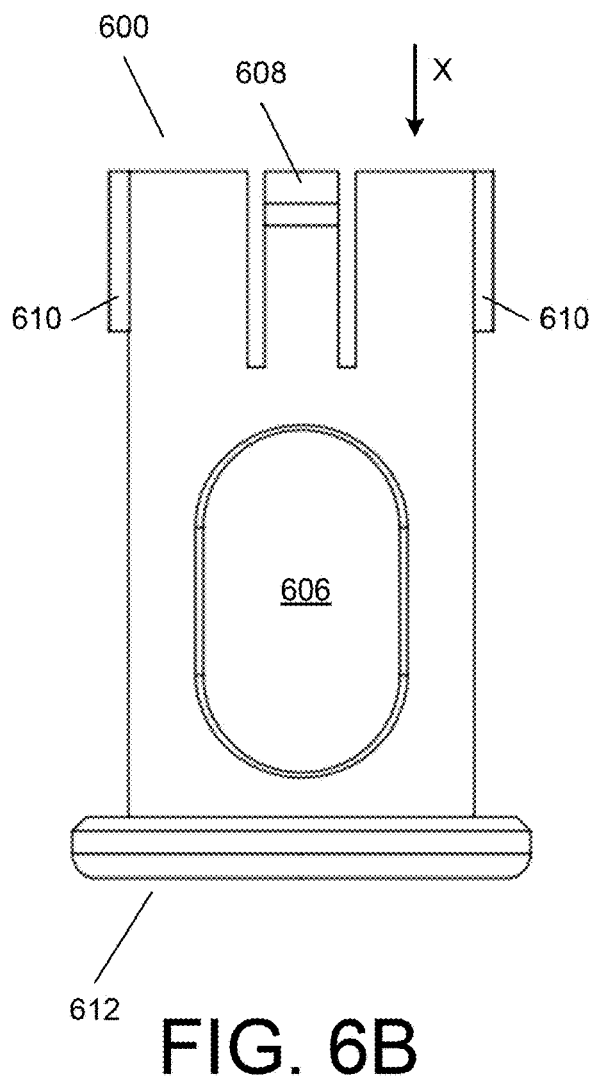

FIG. 6B is a side view of the interior subassembly 600 of FIG. 6A.

Figure 6C:
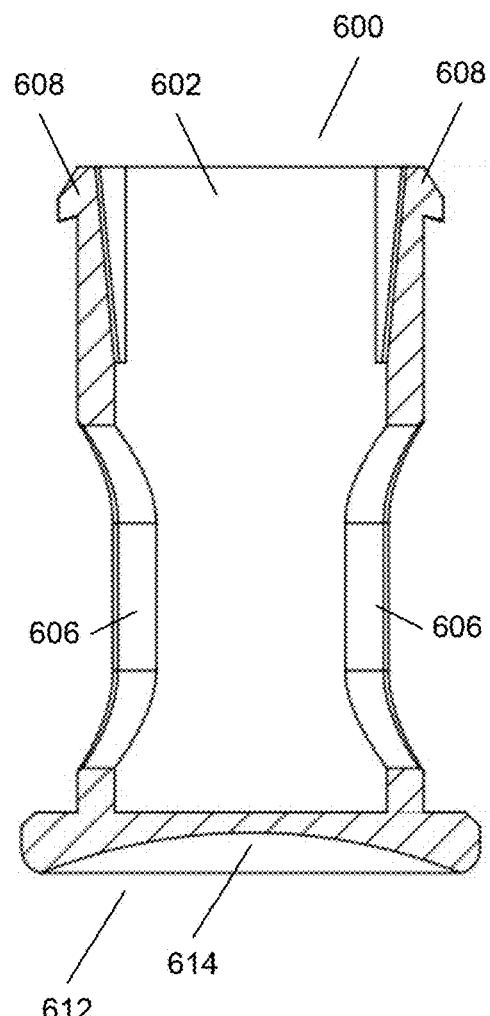

FIG. 6C is a cross section of the interior subassembly 600 of FIG. 6A taken at C-C of FIG. 6A.

As can be seen in this view, the distal end 612 includes an optional concave depression 614, however, some implementations may use a roughened or specific type of surface material to minimize the risk of slippage between a user's thumb and the distal end 612.

Figure 6D:
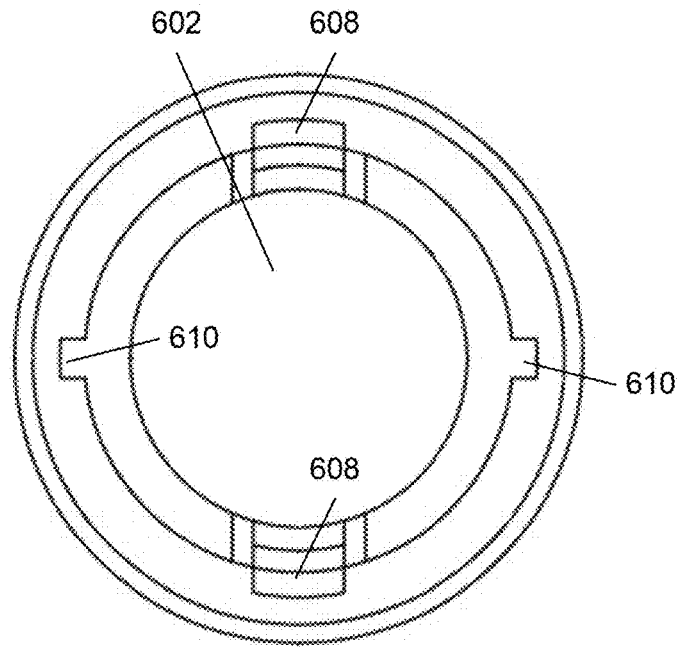

FIG. 6D is an end-on view of the interior subassembly 600 of FIG. 6A viewed in the direction of the arrow "X" in FIG. 6B.

Figures 7A, 7B:
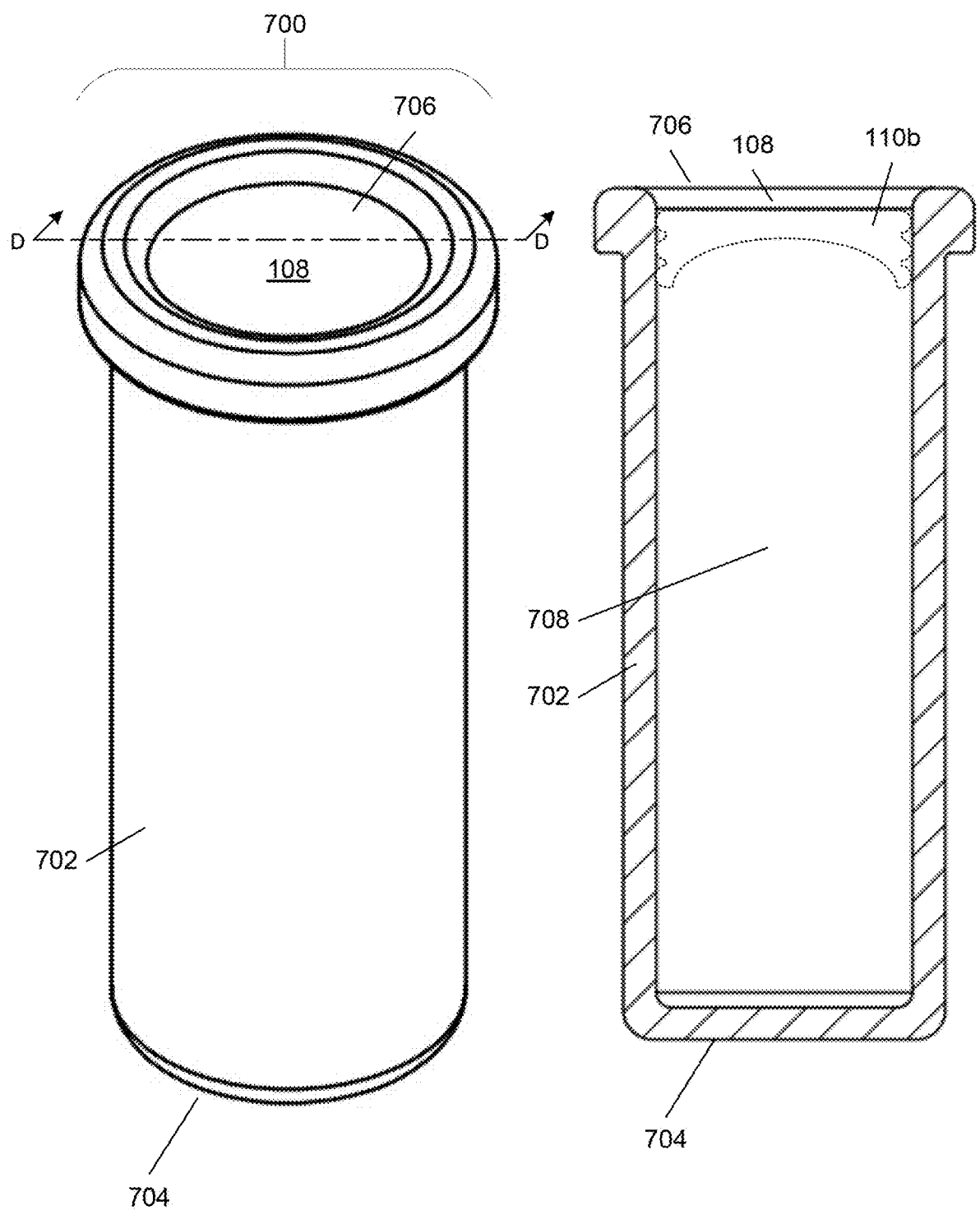
FIGS. 7A-7B depict two views of a vial, similar to the vial of FIGS. 1A-1D, suitable for use with the exterior subassembly of FIG. 3 and interior subassembly of FIG. 6A.

FIGS. 7A-7B depict two views of a vial 700, similar to the vial 102 of FIGS. 1A-1D, suitable for use with the exterior subassembly 300 of FIG. 3 and interior subassembly 600 of FIG. 6A.

Specifically, FIG. 7A is a front perspective view of a vial 700 suitable for use with the exterior subassembly 300 of FIG. 3 and interior subassembly 600 of FIG. 6A.

FIG. 7B is a cross section of the vial 700 of FIG. 7A taken at D-D of FIG. 7A.

As can be seen in these views, vial 700 is cylindrical with the side 702 and distal end 704 being solid such that the only place that medication can enter into, or leave, the vial 700 is through its proximal end 706.

As previously described, when filled with medication, a seal 108 or plunger similar to the plunger 110b of FIGS. 1C-1D is used to contain the medication within the interior cavity 708 of the vial 702. With some implementations, the vial 700 will be made of a plastic with a glass coating applied to its inner surface to better seal the medication or other contents against contamination. With other implementations, the vial 700 may be made completely of glass, completely of plastic, or another suitable material or combination of materials, depending on considerations of a desired shelf-life, risk of interaction of the contents with the vial materials, and/or cost of materials. In other words, the particular material that would be selected for the vial is a matter of design choice appropriate to the intended contents and desired shelf life, the specifics of which are not germane to understanding the teachings herein.

Likewise, the volume of the vial 700 will be a function of the dose to be administered using the particular injection delivery device. For example, the vial 700 shown has an example fillable internal volume 708 of 1 milliliter (1 cubic centimeter), enabling it to be used to administer a dose of a medication of 1 milliliter or less depending upon how much it is filled, or how far the vial 700 is allowed to move relative to the particular plunger. Of course, if larger doses of a medication are to be administered using the teachings herein, the sizes of at least the exterior subassembly 300, interior subassembly 600 and vial 700 would be scaled in the longitudinal direction and/or width direction (i.e., direction perpendicular to the longitudinal direction) in the appropriate manner.

As previously discussed in connection with the vial 102 of FIGS. 1A-1D, the vial 700 is preferably sealed with a vial seal 108 and/or sealing plunger 110b that can be pierced by a component, as previously discussed, during initiation of an injection and, in either case, thereby permits a plunger 110a, 110b to enter and traverse the interior of the vial 700 and cause the medication to be delivered to the proximal end of the needle through the opening created in the seal.

Having described the various components of one example manual injection syringe 200 employing the teachings herein, the process of assembling that manual injection syringe 200 using the foregoing components will now be provided.

The assembly and use of such an example manual injection syringe 200 will now be described with reference to FIGS. 8A-8F.

FIGS. 8A-8C specifically depict example processes for assembling the manual injection syringe 200 of FIG. 2.

The first example assembly process proceeds as follows:

One part of the process involves inserting the medication-containing vial 700 into the interior subassembly 600 to form a first major subcomponent 800 (as shown in FIG. 8A). Another part of the process generally involves attaching a needle 514 to the aperture 308 of the exterior subassembly 300 and then attaching the needle shield 400 to the exterior subassembly 300 so as to cover the needle 514 to form a second major subcomponent 802.

Then, as shown in FIG. 8B, the first major subcomponent 800 is inserted into the second major subcomponent 802 such that the locking features between the interior subassembly 600 and exterior subassembly 300 engage to prevent them from being disconnected. Upon insertion of the interior subassembly 600 portion of the first major subcomponent 800 into the exterior subassembly 300 of the second major subcomponent 802, the distal tip or spike of the needle 514 may be partially piercing the vial seal 108 or plunger 110b, or may be placed in close proximity thereto (i.e., in the interest of compactness, abutting or nearly abutting it, but the actual distance between the two is, again a function of the particular design criteria, and unimportant for understanding the operation), thereby keeping the contents of the vial safe from contamination.

At this point, it is worth noting that, for some implementations, during assembly, a rubber booty (not shown) may optionally be placed over the needle tip at the proximal end to maintain sterility of the needle itself. Similarly, in some implementations, the distal end 118 of the needle or spike may optionally be partially embedded within the vial seal 108 or plunger 110b (if the vial seal 108 or plunger 110b is thick enough) to maintain its sterility as well.

At this point, the manual injection syringe 200 is assembled and ready for use or packaging for distribution or sale, and later use.

At this point, it should be noted that individual assembly of the first major subcomponent 800 and the second major subcomponent 802 can occur in any order, or can occur concurrently.

The second example assembly process is similar to the first with respect to creation of the first major subcomponent 800. However, with this alternative process, the first major subcomponent 800 is then coupled to the exterior subcomponent 300. Thereafter, the needle 514 and needle shield 400 are attached.

As a result of the foregoing, as shown in FIG. 8C, the final, assembled manual injection syringe 200 is the result.

It should now be appreciated that manual injection syringe 200 has few discrete parts, can easily be manufactured, and is simple to assemble.

With continuing reference to FIG. 8C and additional reference to FIGS. 8D-8F, the manipulation of the assembled manual injection syringe 200 for use and disposal will now be described.

Returning now to FIG. 8C, the process for use begins with the movement of the needle shield 400 of the manual injection syringe 200 in the direction shown by the arrow. This results in a configuration as shown in FIG. 8D, where at least the proximal end of the needle 514 is exposed to allow the injection to proceed. Following insertion of the needle 514 into the injection target (not shown), pressure is applied by a user to the distal end 610 of the interior subassembly 600 of the manual injection syringe 200 in the direction of the arrow of FIG. 8D, while the user constrains the body of the manual injection syringe 200 between their fingers using the finger grips 304 until the first major subcomponent 800 reaches the specified stop, as previously described in connection with FIGS. 1B, 1D. This is shown in FIG. 8E.

More particularly, as the first major subcomponent 800 moves proximally, the distal end of the needle 118 pierces the vial seal 108 (or plunger 110b if it performs that function) and then, as more pressure is applied to the first major subcomponent 800 (i.e., combined interior subassembly 600 and vial 700), the first major subcomponent 800 will move proximally while the needle 514 and plunger remain fixed in place by the exterior subassembly 300. This relative movement reduces the available volume of the vial 700, compresses the medication within the vial 700, and causes flow of medication through the needle 514. As injection concludes, the vial 700 will have moved such that the vial seal 108 or plunger 110b will have traversed most, if not all, of the longitudinal depth of the vial 700.

It should now be appreciated that, in some implementations, the relatively free movement of the needle shield 400 along the exterior surface of the exterior subassembly 100 allows the manual injection syringe 200 to be pressed against skin at the target location to insert the needle 512 into the target location without requiring a separate action to move the needle shield 400. Alternatively, in other implementations, the needle shield 400 may be retracted, in whole or part, by action of a spring or other mechanical component, although such a configuration will require additional parts and add complexity.

At this point, the injection is complete.

Thereafter, the manual injection syringe 200 is withdrawn and, depending upon the particular implementation, the needle shield 400 will be moved, in the direction of the arrow of FIG. 8F, until it reaches its terminal "locked" position, thereby fully enclosing the needle 514 again. As will now be understood, with some implementations, this would be done manually by the user, whereas with other implementations, this could be performed, in whole or part, by action of a spring or other mechanical component.

At this point, the used syringe 200 can be easily disposed of.

Of course, it should be understood that, implementations of the foregoing can readily be created such that some or all of the sub components 300, 400, 600 can be made from materials that allow them to be re-sterilized and re-used. Advantageously, such implementations can be created without meaningfully changing the complexity, other than, perhaps providing additional holes or other means to allow the tabs or other mechanisms to be manipulated for disassembly.

Figure 9:
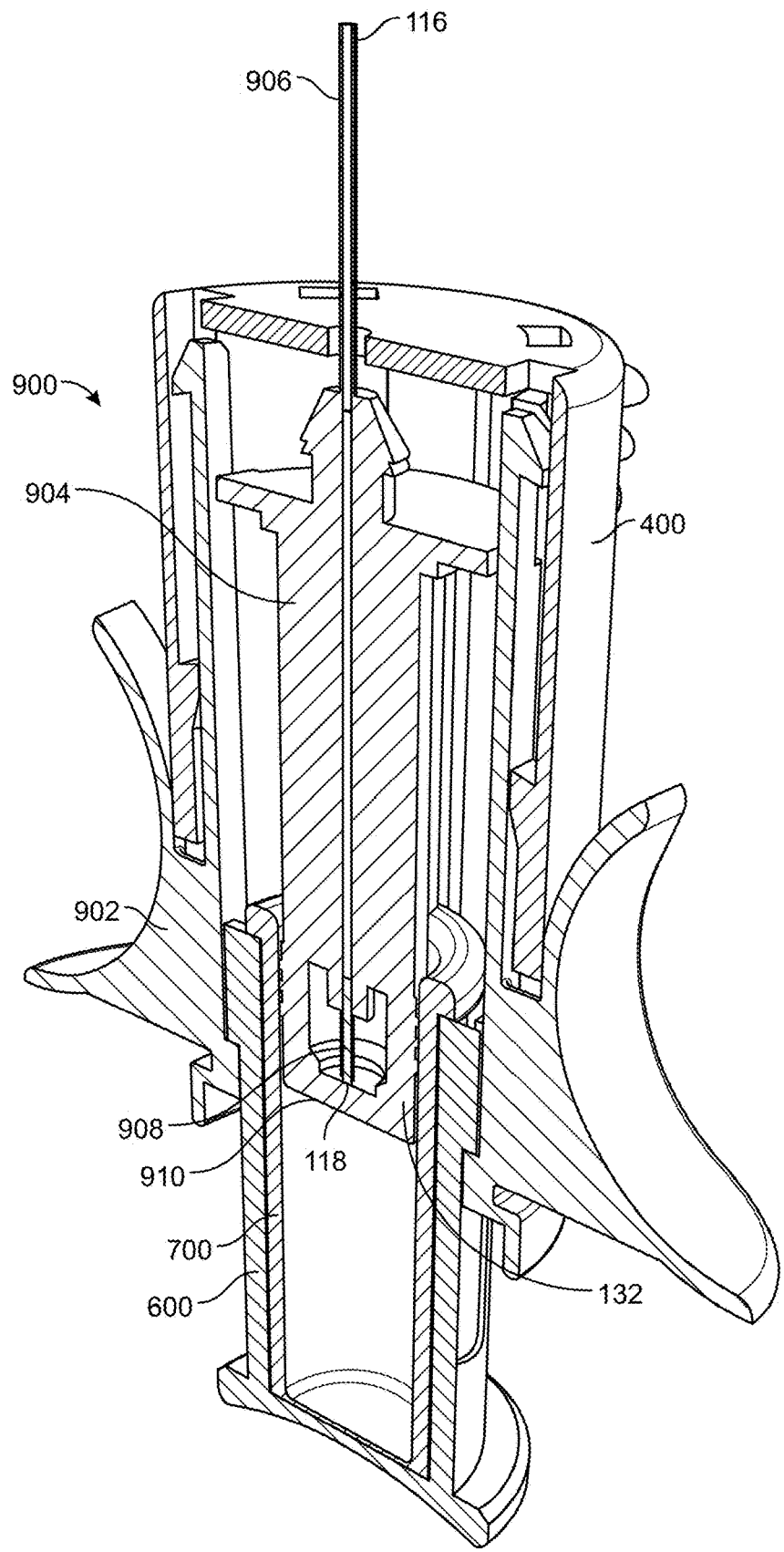
FIG. 9 illustrates, in simplified form, a cross section of a manual injection syringe that is similar to the manual injection syringe of FIG. 2.

FIG. 9 illustrates, in simplified form, a cross section of a manual injection syringe 900 that is similar to the manual injection syringe 200 of FIG. 2. However, unlike the manual injection syringe 200 of FIG. 2, the exterior subcomponent 300 may be made up of two parts, an external housing 902 and an insert 904 comprising the plunger engagement feature 132. With this configuration, the exterior subcomponent 300 is created by inserting the insert 904 into the external housing 902 and affixed in place, for example, through ultrasonic welding or other form of mechanical attachment approach, such as tabs, a bayonet connection, etc., the manner of attachment being one of design choice.

Alternatively, as shown in FIG. 3B, the external housing 902 and an insert 904 could be directly formed as a single unit.

In addition, and unlike the exterior subcomponent 300 of FIGS. 3A-3E where a single needle 514 may pass through the entire length of the exterior subassembly 300, with the implementation of FIG. 9, there is a discrete passage 902 formed within the insert 904 that longitudinally passes through the entire insert 904. In such a configuration, the needle 514 effectively comprises a first needle 906 affixed to the proximal end of the passage 902 for purposes of insertion into the skin for the injection, and a second element 908 (i.e., another needle, spike or other hollow puncturing element at the distal end 910, that is used to pierce into the vial 700 and permit flow of medication through the passage 902 to and through the proximal tip 116 of the needle 906.

It is to further be understood, for all configurations described herein, that for the hollow puncturing element on the distal end (e.g., spike or needle), the opening in that puncturing element need not be at the very distal tip. For example, as shown above in FIGS. 1A-1B, a conical structure may be used that has a sharp tip with one or more opening(s) 124 removed from the very tip, so that only after the tip pierces into the vial 700, will the opening(s) 124 enter the vial 700 and be in fluid communication with the medication to then permit the medication to exit the vial 700 therethrough.

FIGS. 10A-10E show various views of other example manual injection syringe 1000a, 100b implementations incorporating the teachings herein.

Figure 10A:
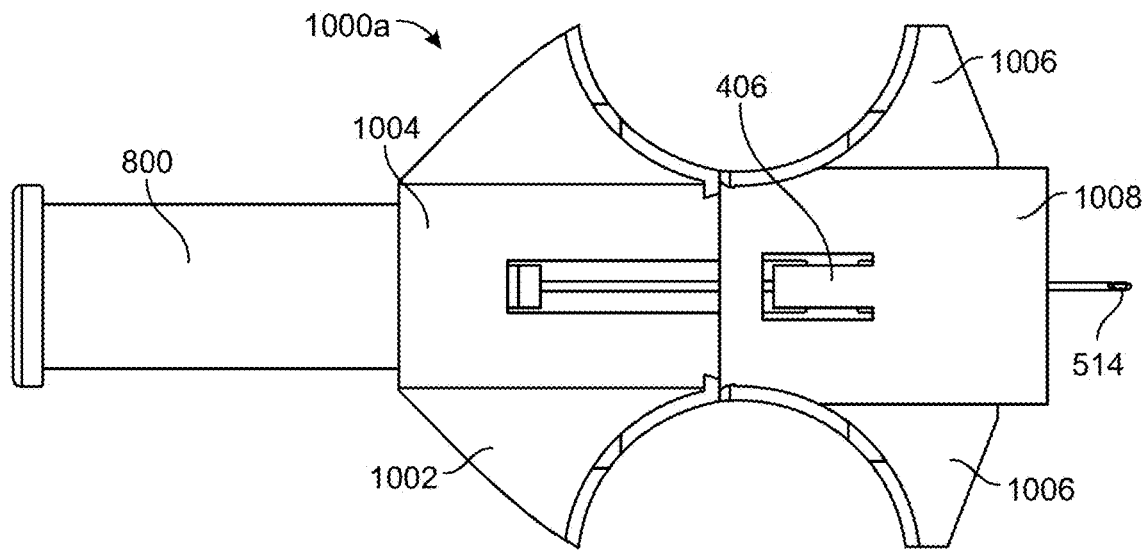
FIGS. 10A-10E show various views of other example manual injection syringe implementations incorporating the teachings herein.

Specifically, FIG. 10A shows one alternative example manual injection syringe 1000a implementation, incorporating the teachings herein. As depicted in FIG. 10A, this manual injection syringe 1000a includes a pair of distal finger grips 1002 on the exterior subassembly 1004 and a pair of proximal finger grips 1006 on the needle shield 1008 (which is shown as already retracted to reveal the needle 514).

Optionally, with some alternative versions of this implementation, the distal end of the interior subassembly 600 can have a thumb ring to make operation of this variant easier.

In all other meaningful respects, the internal structure of this variant 1000a is similar to those previously described herein.

Figure 10B:
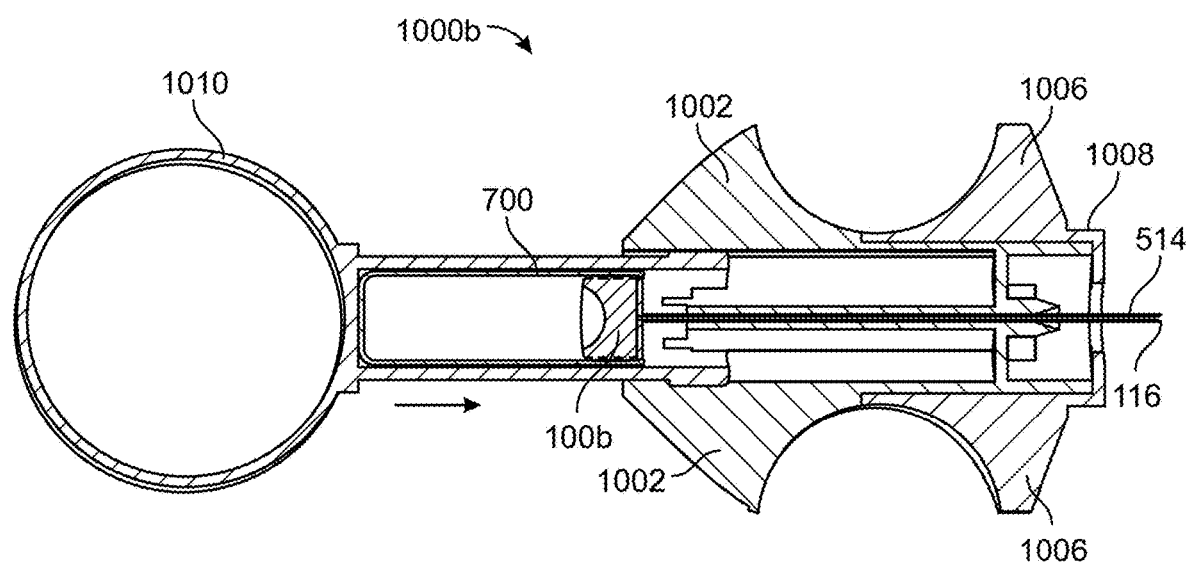

FIG. 10B is a cross section of another alternative example manual injection syringe 1000b implementation, incorporating the teachings herein that is identical to the manual injection syringe 1000a of FIG. 10A, except that it includes a thumb ring 1010. As with FIG. 10A, the needle shield 1008 is shown as already retracted to reveal the needle 514. Thus, as shown, the manual injection syringe 1000b is ready to initiate an injection.

To provide the injection, the user grips the finger grips 1002 and thumb ring 1010 and applies a force directed towards bringing the thumb ring 1010 towards the finger grips 1002. This causes the medication-containing vial 700 to move proximally (as shown by the arrow in FIG. 10B) towards the needle 514 so that the distal end of the needle 118 initially pierces the plunger 110b and then drives the vial 700 further onto the stopper causing the medication to exit the vial 700 via the distal end 118 of the needle 514 and be forced towards the proximal end 116 of the needle 514.

Figure 10C:
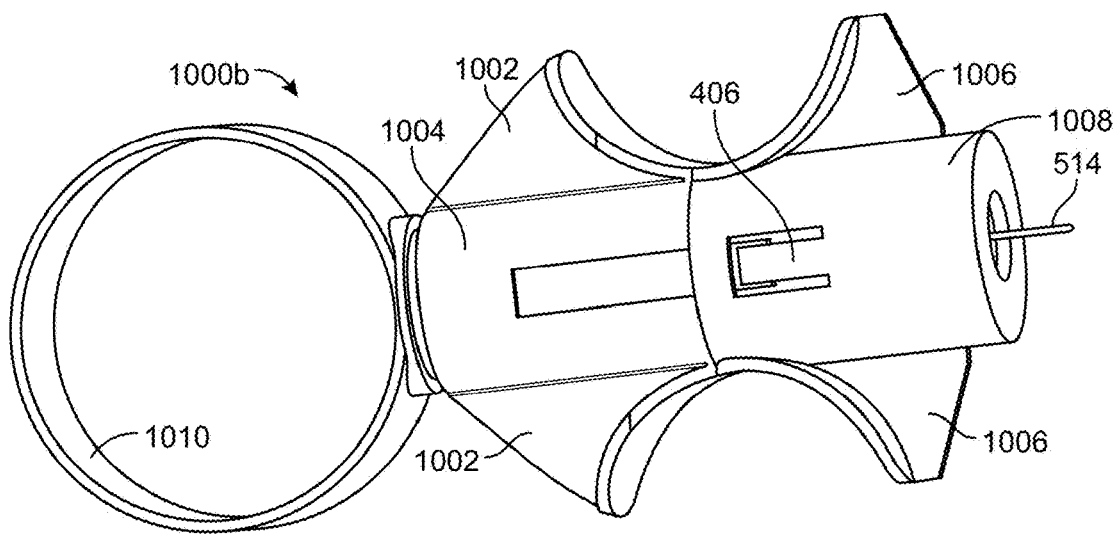

FIG. 10C shows the manual injection syringe 1000b after the full injection has been delivered. As a result, with this manual injection syringe 1000b, the vial 700 is now positioned fully within the exterior subassembly 1004. More particularly, when the interior subassembly 600 containing the vial 700 is fully depressed so that it has moved to its proximal limit within the exterior subassembly 1004, two or more internal tabs therein are able to move into a recess formed therein and thereby lock the interior subassembly 600 and exterior subassembly 1004 together, immobilizing the two subassemblies with respect to one another. Moreover, with this implementation, the movement of the interior subassembly 600 displaces the one or more fingers 406 of the needle shield 1008 that had previously locked the needle shield 1008 in place when it was retracted to the position shown in FIG. 10A. As a result, the needle shield 1008 is able to be extended to enclose the needle 514.

Figure 10D:
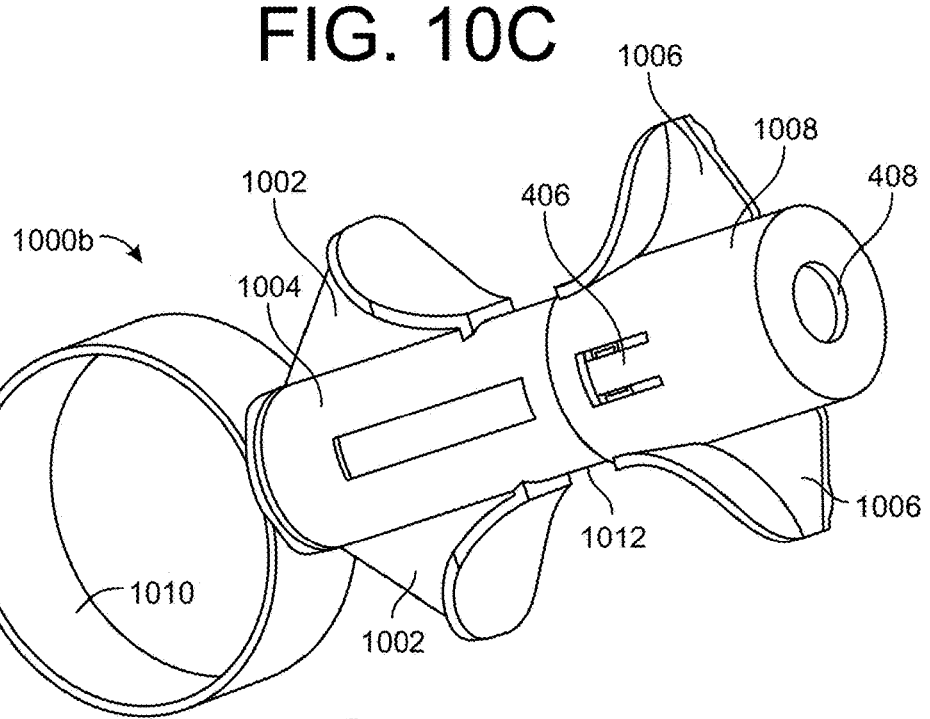

FIG. 10D shows the manual injection syringe 1000*b* after the needle shield 1008 has been extended or re-deployed. As shown in FIG. 10D, re-deployment of the needle shield 1008 is accomplished, at the conclusion of the injection once the one or more fingers 406 of the needle shield 1008 are displaced, by the user extending their fingers forward (i.e., proximally as shown by the arrow of FIG. 10B) to engage with the proximal grips 1006 while concurrently applying a backward force to the thumb ring 1010. This causes the needle shield 1008 to move proximally away from the exterior subassembly 1004, creating a space 1012 between them. The needle shield 1008 will then lock into place when the fingers 406 have engaged with corresponding proximal indentations of the exterior subassembly 1004 so that the needle shield 1008 will be locked in an extended position where it encloses the needle 514 (as depicted in FIG. 10D).

Figure 10E:
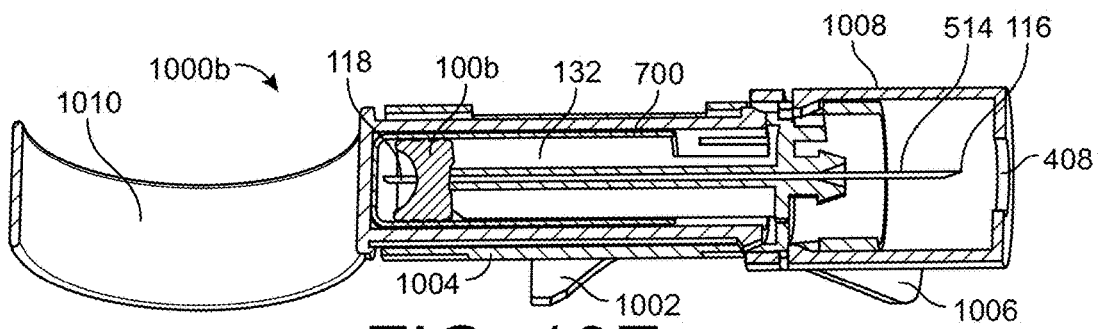

FIG. 10E is a cross section of the manual injection syringe 1000*b* of FIG. 10D to show the relative positions of the internal components.

Figure 11:
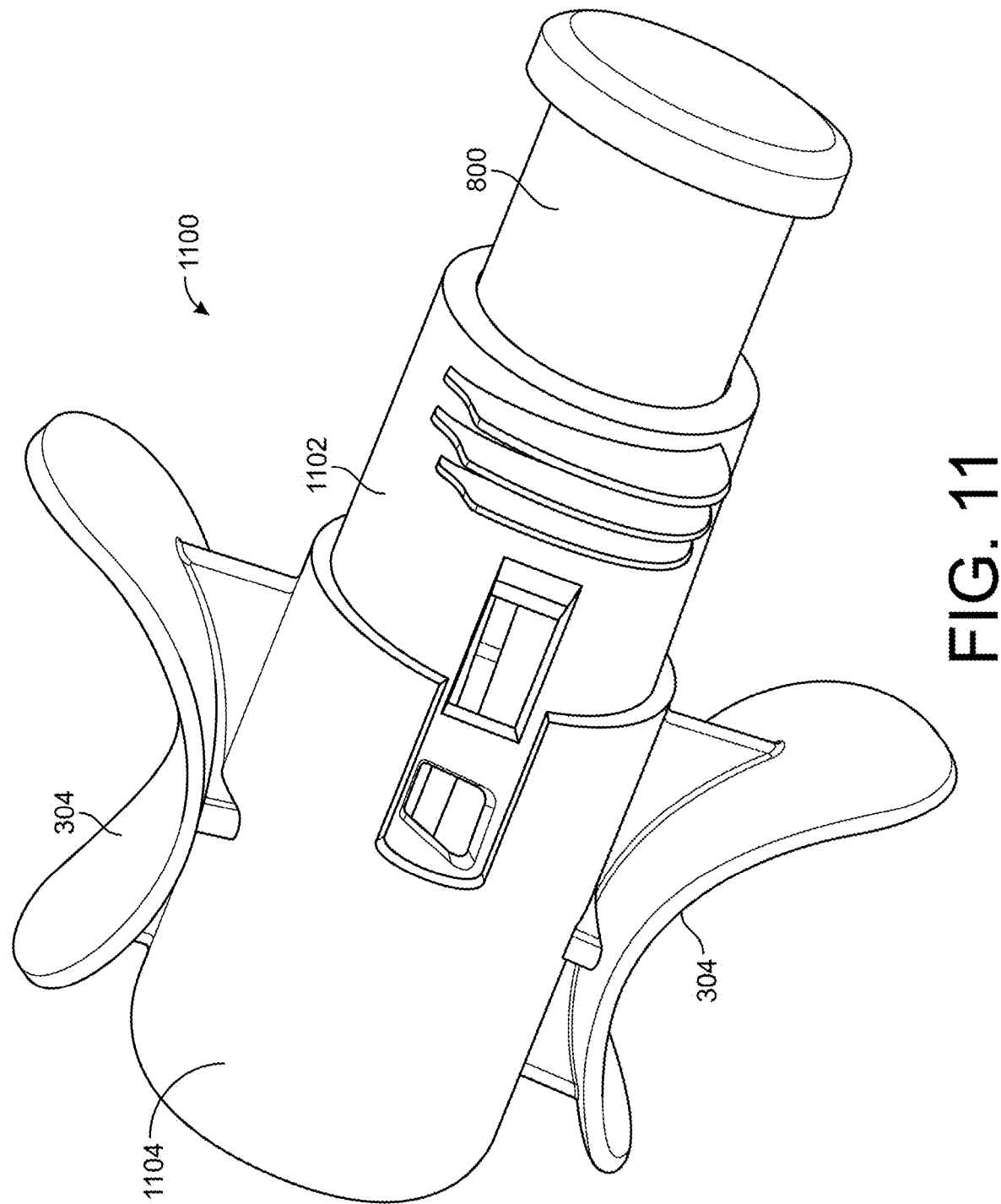
FIG. 11 is a perspective view of another alternative variant design of a manual injection syringe.

FIG. 11 is a perspective view of another alternative variant design of a manual injection syringe 1100.

In the variant 1100 of FIG. 11, the exterior subassembly 1102 does not have any finger grips. Rather, the finger grips 304 are affixed to the needle shield 1104, permitting the user to retract the needle shield in preparation for an injection by applying an initial retracting force distally using the finger grips 304 while the user applies an opposite force against the distal end of the first major subcomponent 800 with their thumb. In all other material respects (i.e., the operation as discussed in connection with FIGS. 1A-1B or FIGS. 1C-1D), the internal operation of this variant 1100 is the same as described therein. Thus, once the needle shield 1104 is fully retracted, continued application of force to the distal end of the first major subcomponent 800 with the user's thumb will thereafter cause the piercing of the vial seal and delivery of medication from the vial as described above.

Additionally, some further variants may include a spring or other source of a biasing force so that the user is not actively applying a force to retract the needle shield 1104 or continuing to apply a force to deliver the injection, the spring or other source of a biasing force will automatically re-deploy (i.e., extend) the needle shield 1104 so that it covers the needle.

Up until now, various different alternative implementations of injection delivery devices, in the form of manual injection syringes, have been discussed in order to demonstrate the principles of operation and some of the many configurations that can be created while using the principles taught herein. However, advantageously, injection delivery devices employing the teachings herein are not so limited. As will now be seen, these same teachings can also be employed in injection delivery device implementations that are autoinjectors.

FIGS. 12A-12E are various views of one example autoinjector 1200 employing the teachings herein.

Figures 12A, 12B:
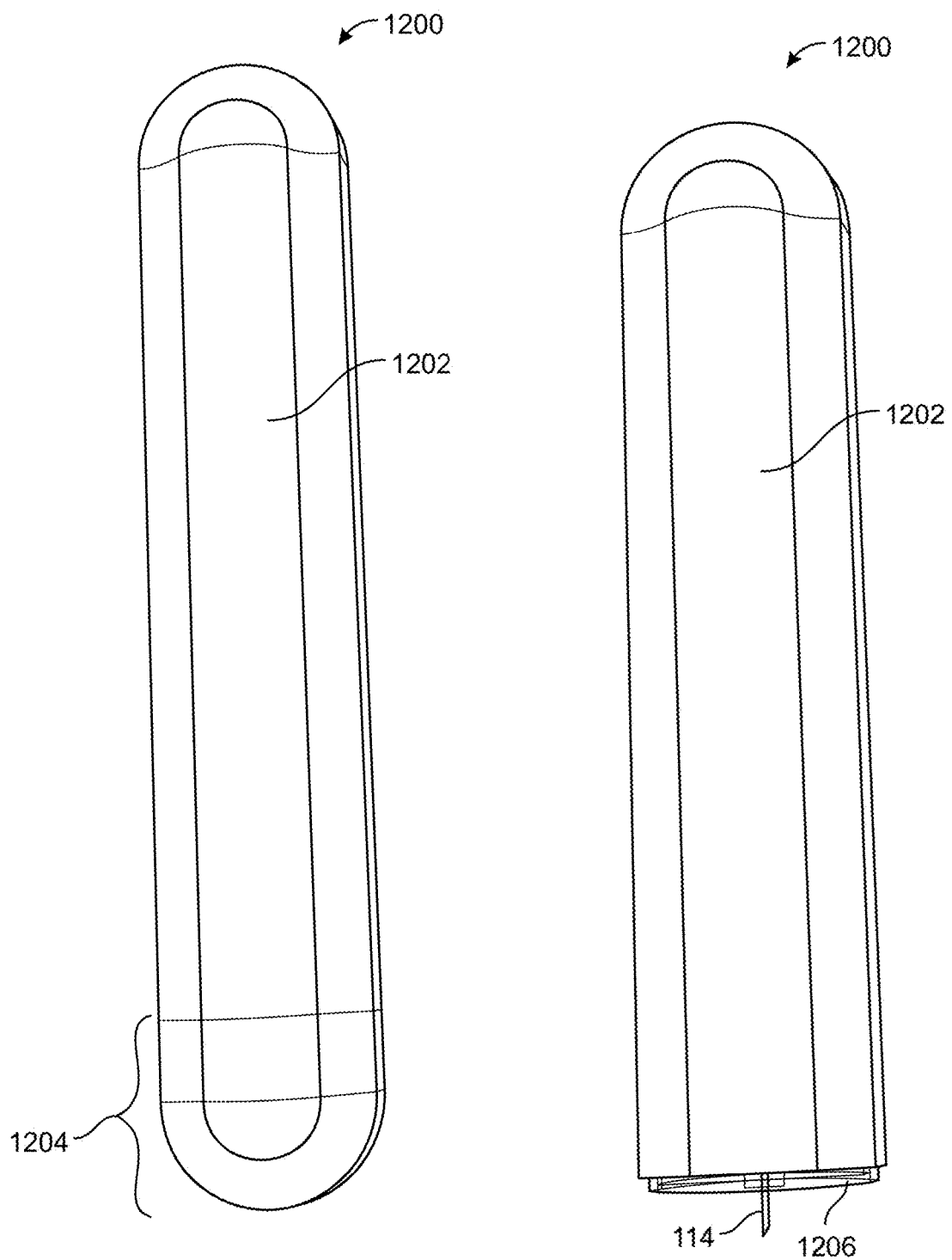
FIGS. 12A-12E are various views of one example autoinjector employing the teachings herein.

Specifically, FIG. 12A is an external view of one example autoinjector constructed to operate according to the principles described above with respect to manual injection syringes.

As shown in FIG. 12A, the example autoinjector 1200 comprises an external housing 1202 and a protective cap 1204.

FIG. 12B shows the autoinjector 1200 of FIG. 12A after removal of the cap 1204 in preparation for use, exposing a needle 114 and, for purposes of explanation, a needle shield 1206 that is in its retracted position to expose the needle 114.

Figure 12C:
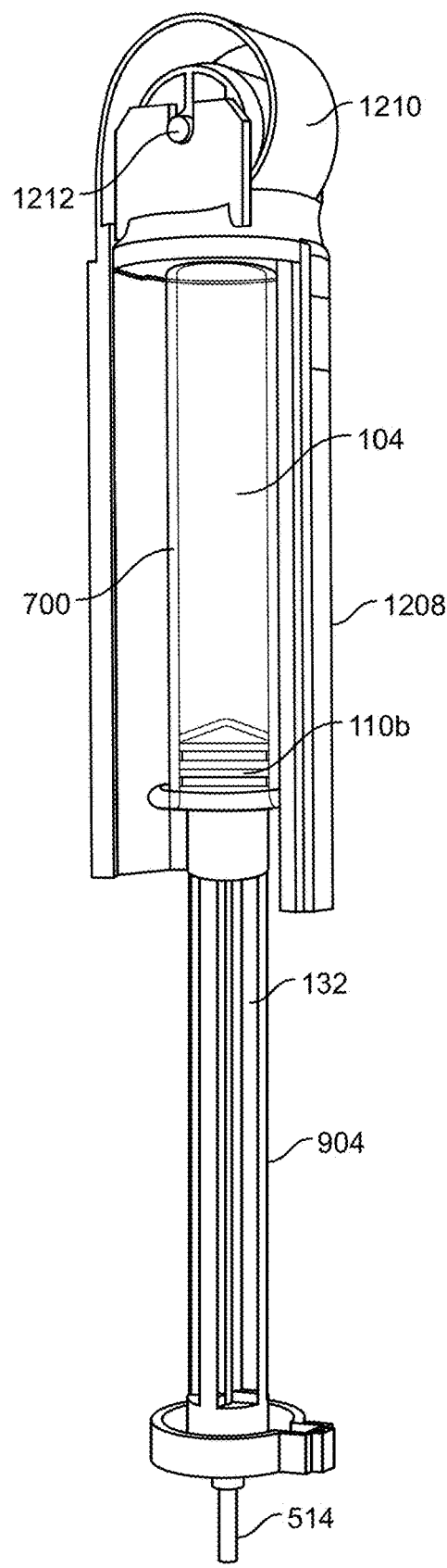

FIG. 12C is a partial view of the internal components of the autoinjector 1200 of FIG. 10A as they would be immediately before an injection begins.

As shown in FIG. 12C, the autoinjector 1200 has an interior subassembly 1208 within which a medication-containing vial 700 is positioned. The interior subassembly 1208 further includes a constant force spring 1210, which is wound about a center axle 1212, as commonly used in conventional autoinjectors. The constant force spring 1210 is used to apply a force to the distal end of the vial 700 as it winds itself about the center axle 1212 in the manner a thumb would with the manual injection syringes described above.

As further shown in FIG. 12C, this autoinjector 1200 includes a separate insert 904 that includes the plunger engagement feature 132.

Figure 12D:
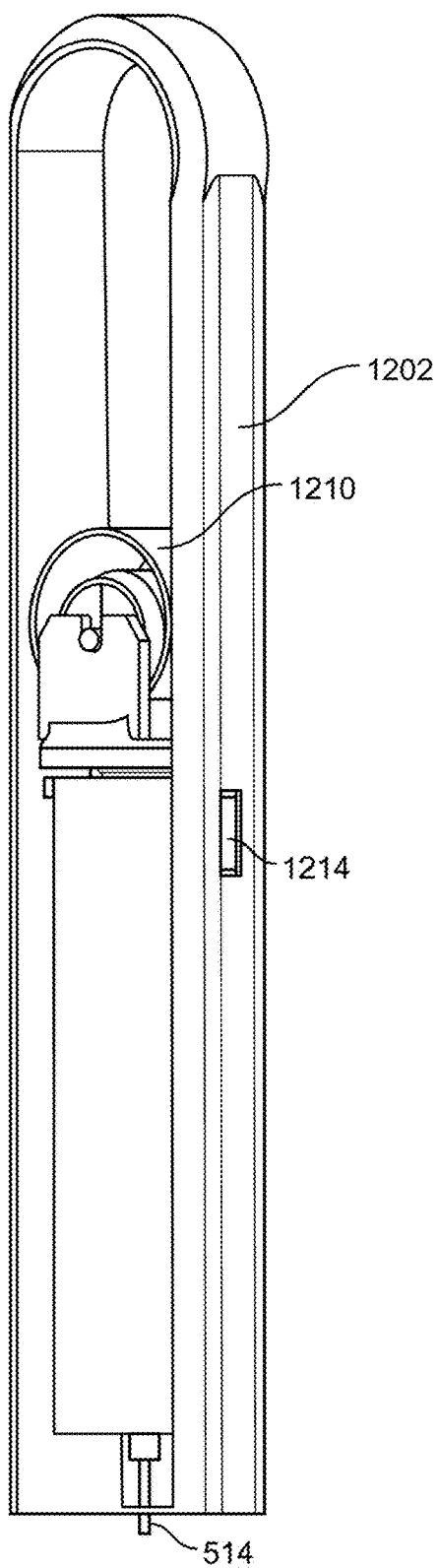

FIG. 12D shows a partial cutaway internal view of the autoinjector of FIG. 12A as an injection is concluding. In operation, the force applied by the constant force spring 1210 causes proximal movement of the interior subassembly 1208, causing the vial 700 to fully enclose the plunger 110*b* and most (if not all) of the plunger engagement feature 132.

Optionally, an indicator 1214 may be provided on the surface of the interior subassembly 1208 such that it is not visible before the injection is performed, but the indicator 1214 becomes visible, for example, through an opening in the housing 1202 to indicate that the dose of medication has been fully delivered and the autoinjector can be discarded. Alternatively, an indicator can be provided that appears one way prior to the injection, but movement of the interior subassembly 1208 to its terminal proximal position will cause the indicator 1214 to change in some manner (e.g., appearance/disappearance, position, make a sound, etc.).

Figure 12E:
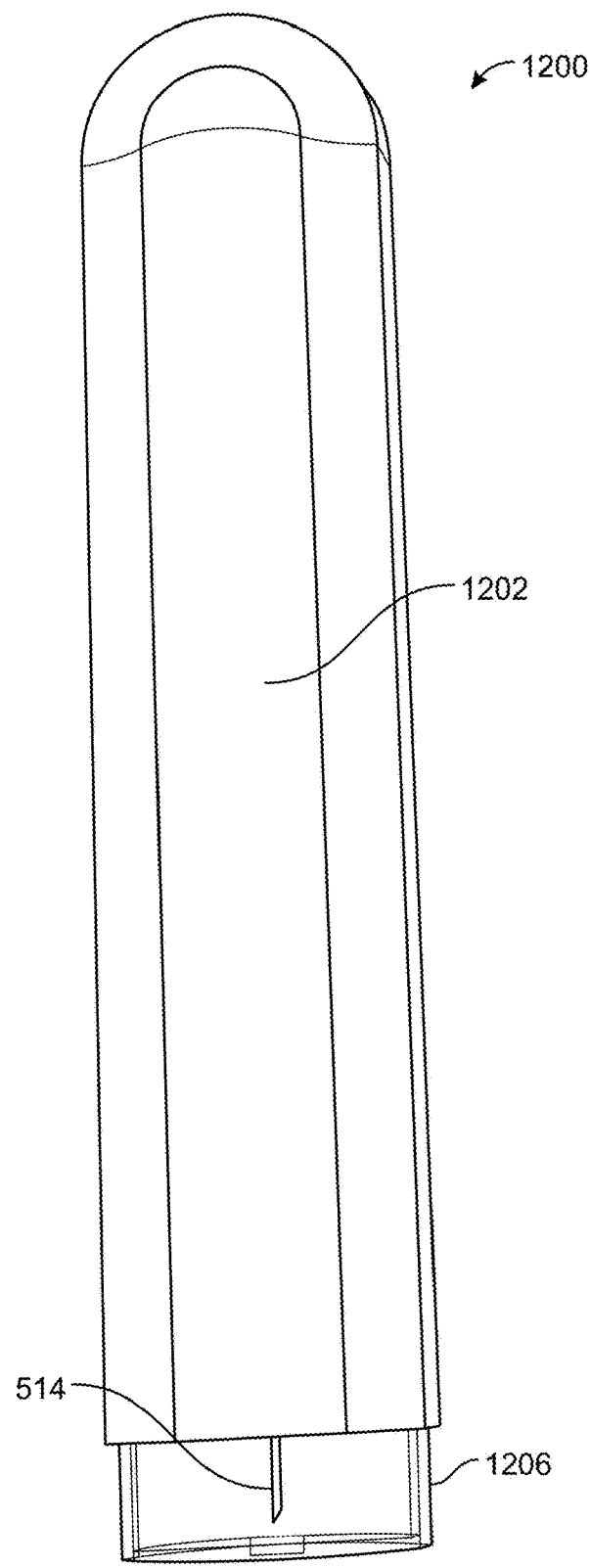

FIG. 12E is an external view of the autoinjector 1200 of FIG. 12A after the needle shield 1206 has been redeployed following completion of the injection. Depending upon the particular implementation, the redeployment of the needle shield 1206 can occur manually when the needle 514 has been removed from the injection target, under the urging of a separate biasing spring, or movement of the interior subassembly 1208 to its full proximal extent by the spring 1210 can also automatically engage with, and push, the needle shield 1206 proximally, thereby concurrently withdrawing the needle 514 and ultimately enclosing the needle 514 therewithin.

Depending upon the particular implementation, various further configurations of autoinjectors can be created using the teachings herein and adding other features commonly found in some autoinjectors. For example, an external button can be provided on the surface of the housing 1202 that can be used to initiate the injection by releasing the spring 1210, allowing the spring 1210 to begin retracting. Alternatively, implementations can be constructed such that distal movement of the needle shield 1206 from pressing the needle shield 1206 against the skin during an injection triggers the spring 1210.

Finally, irrespective of whether an injection delivery device, constructed according to the teachings herein, is a manual injection syringe or an autoinjector, such products may optionally incorporate an RFID tag or other device to uniquely identify it and thereby be used to track distribution and/or use (for example, passing it in front of an RFID scanner upon shipment, delivery, or, in other cases, in conjunction with use to create a link in a database between a particular dose and the time and location of use). Alternatively, other identifiers such as barcodes or other serial numbers may be printed, formed on, or impressed into, any of the previously described components. In still other variants, each vial 700 may have a barcode or other visual identifier on it that can be scanned optically, for example, through windows of the interior and/or exterior subassemblies.

Based upon the foregoing, it should now be appreciated that, although, from the exterior, injection delivery devices constructed according to the teachings herein may superficially have the appearance of a traditional syringe or autoinjector, but, internally, this is not the case.

Rather, unlike conventional syringes (manual or autodelivery) where the medication is contained in a vial or syringe body and is dispensed from one end to a needle by application of pressure to a plunger at the opposite end, according to the teachings herein, the needle and plunger are on the same side of the medication-containing vial and the medication is dispensed through the plunger. Likewise, during injection, rather than a thumb pressing on a plunger to push the plunger into one end of the vial or syringe body so that the medication will be dispensed from the opposite end, according to the teachings herein, during injection, the vial itself is moved while the plunger and needle remain stationary relative to each other at the delivery (proximal) end of the injection delivery device. Thus, according to the teachings herein, the interior subassembly is more accurately considered and "activator" since, at the time of the injection, once medication can enter the needle, the interior subassembly does not move the plunger at all.

Having described and illustrated the principles of this application by reference to one or more examples, it should be apparent that embodiment(s) may be constructed and/or modified in arrangement and detail without departing from the principles disclosed herein and that it is intended that the application be construed as including all such modifications and variations insofar as they come within the spirit and scope of the subject matter disclosed.

The foregoing outlines, generally, the features yielding technical advantages of one or more implementations that can be constructed based upon the teachings in this disclosure in order that the foregoing detailed description would be better understood. However, the advantages and features described herein are only a few of the many advantages and features available from representative examples of possible variant implementations and are presented only to assist in understanding. It should be understood that they are not to be considered limitations on the invention as defined by the appended claims, or limitations on equivalents to the claims. For instance, some of the advantages or aspects of different variants are mutually contradictory, in that they cannot be simultaneously present in a single embodiment. Similarly, some features or advantages may be applicable to one aspect and inapplicable to others. Thus, the foregoing features and their associated advantages should not be considered dispositive in determining equivalence. Additional, unenumerated, features and advantages will also be apparent from the teachings of the description, drawings, and claims.

What is claimed is:

1. An injection delivery device, comprising:
    a body, comprising an interior subassembly and an exterior subassembly;
    a medication-containing vial within at least a portion of the body, the vial having an open end and a closed end opposite the open end, wherein the open end of the vial includes a seal that prevents medication contained therein from exiting the vial until delivery of the medication to a target injection site is desired;
    wherein a side surface of the exterior subassembly includes at least one window therein;
    wherein a side surface of the interior subassembly includes at least one window therein corresponding to the at least one window of the exterior subassembly, so as to permit viewing of the vial from outside the exterior subassembly;
    a plunger positioned near the open end of the vial;
    a needle having a first end and a second end and a passage therethrough, the first end of the needle being usable for insertion into skin of a target injection site, and the second end of the needle being positioned to direct the medication from the vial into the passage for delivery to the target injection site via the first end; and
    wherein the needle, the plunger and the vial are all linearly coaxially aligned and positioned relative to each other such that, during delivery of an injection, a portion of the passage will be within the plunger, and the plunger and the needle will remain stationary relative to each other while the vial moves relative to the plunger in a direction towards the target injection site.

2. The injection delivery device of claim 1, wherein the second end of the needle comprises an angle cut needle end.

3. The injection delivery device of claim 1, wherein the plunger is affixed to the needle.

4. The injection delivery device of claim 1, wherein a portion of the plunger is the seal; prior to injection, at least a portion of the plunger is within the vial; and the second end of the needle is positioned to, upon initiation of the injection, pierce the portion of the plunger that is the seal.

5. The injection delivery device of claim 4, further comprising a plunger engagement feature.

6. The injection delivery device of claim 5, wherein the plunger engagement feature is one of a plate, a post, a protrusion, or an expanded region, associated with the needle.

7. The injection delivery device of claim 1, wherein the vial is contained within the internal subassembly.

8. The injection delivery device of claim 5, wherein the plunger engagement feature is part of the body.

9. The injection delivery device of claim 5, wherein the plunger engagement feature is part of an insert fixedly coupled to the body.

10. The injection delivery device of claim 1, further comprising at least one finger grip coupled to an exterior surface of the body.

11. The injection delivery device of claim 1, further comprising a needle shield near the first end of the needle.

12. The injection delivery device of claim 11, wherein the needle shield is slidably movable relative to the body.

13. The injection delivery device of claim 12, wherein the needle shield includes at least one finger positioned to constrain the needle shield, when in a first position, such that the needle shield is covering the needle; and when in a second position, such that the needle is exposed.

14. The injection delivery device of claim 13, further comprising at least one finger grip on the needle shield.

15. The injection delivery device of claim 1, wherein the injection delivery device is an autoinjector.

\* \* \* \* \*